United States Patent
Seo

(10) Patent No.: US 10,639,170 B2
(45) Date of Patent: May 5, 2020

(54) TORQUE OUTPUT TIMING ADJUSTMENT METHOD AND APPARATUS

(71) Applicant: Samsung Electronics Co., Ltd., Suwon-si, Gyeonggi-do (KR)

(72) Inventor: Keehong Seo, Seoul (KR)

(73) Assignee: Samsung Electronics Co., Ltd., Gyeonggi-Do (KR)

(*) Notice: Subject to any disclaimer, the term of this patent is extended or adjusted under 35 U.S.C. 154(b) by 979 days.

(21) Appl. No.: 15/189,559

(22) Filed: Jun. 22, 2016

(65) Prior Publication Data
US 2017/0128235 A1    May 11, 2017

(30) Foreign Application Priority Data
Nov. 11, 2015  (KR) .................. 10-2015-0158199

(51) Int. Cl.
| | | |
|---|---|---|
| *B25J 9/00* | (2006.01) | |
| *A61F 2/60* | (2006.01) | |
| *A61F 2/68* | (2006.01) | |
| *A61F 5/01* | (2006.01) | |

(52) U.S. Cl.
CPC ............. *A61F 2/605* (2013.01); *A61F 2/68* (2013.01); *A61F 5/0102* (2013.01); *B25J 9/0006* (2013.01); *A61F 2002/608* (2013.01)

(58) Field of Classification Search
CPC ........ B29C 33/38; A61F 2/2875; A61F 2/605; A61F 2/60; A61F 2/68; A61F 5/0102; A61H 2003/007; A61H 3/00; B25J 9/0006
See application file for complete search history.

(56) References Cited

U.S. PATENT DOCUMENTS

| | | |
|---|---|---|
| 8,512,415 B2 | 8/2013 | Herr et al. |
| 2005/0177080 A1* | 8/2005 | Yasuhara ............... A61B 5/112 602/16 |
| 2012/0259430 A1 | 10/2012 | Han et al. |
| 2014/0088727 A1 | 3/2014 | Han et al. |
| 2015/0127018 A1 | 5/2015 | Lim et al. |

FOREIGN PATENT DOCUMENTS

| | | |
|---|---|---|
| JP | 4611580 B2 | 1/2011 |
| JP | 5640991 B2 | 12/2014 |
| JP | 5747357 B2 | 7/2015 |
| KR | 20150049856 A | 5/2015 |
| KR | 20150083331 A | 7/2015 |

* cited by examiner

*Primary Examiner* — Suba Ganesan
(74) *Attorney, Agent, or Firm* — Harness, Dickey and Pierce, P.L.C.

(57) ABSTRACT

Provided is a torque output timing adjustment method and apparatus, wherein an assistance power provided by a walking assistance apparatus is determined based on an output assistance power and a joint angle rate, a pattern of a joint angle rate varies for each user based on a gait pattern varying for each user, and an assistance torque provided to a user is adjusted in response to an adjustment of a torque output timing.

18 Claims, 21 Drawing Sheets

TORQUE OUTPUT TIMING ADJUSTMENT METHOD AND APPARATUS

CROSS-REFERENCE TO RELATED APPLICATION

This application claims under 35 U.S.C. § 119 to Korean Patent Application No. 10-2015-0158199, filed on Nov. 11, 2015, in the Korean Intellectual Property Office, the entire contents of which are incorporated herein by reference in its entirety.

BACKGROUND

1. Field

At least one example embodiment relates to a walking assistance method and/or apparatus, and more particularly, to a method and/or apparatus for adjusting a torque output timing.

2. Description of the Related Art

With the onset of rapidly aging societies, a number of people may experience inconvenience and/or pain from joint problems. Thus, there is a growing interest in walking assistance devices enabling the elderly and/or patients having joint problems to walk with less effort. Furthermore, walking assistance devices increasing muscular strength of human bodies may be desired for military purposes.

In general, walking assistance devices may include body frames disposed on trunks of users, pelvic frames coupled to lower sides of the body frames to cover pelvises of the users, femoral frames disposed on thighs of the users, sural frames disposed on calves of the users, and/or pedial frames disposed on feet of the users. The pelvic frames and femoral frames may be connected rotatably by hip joint portions, the femoral frames and sural frames may be connected rotatably by knee joint portions, and/or the sural frames and pedial frames may be connected rotatably by ankle joint portions.

SUMMARY

Some example embodiments relate to a method of adjusting a torque output timing of a torque output by a walking assistance apparatus to a leg of a user.

In some example embodiments, the method includes detecting a joint angle rate interval in which a joint angle rate of the leg of the user is maximized in a gait cycle of the leg; detecting an assistance power interval in which an assistance power applied from the walking assistance apparatus to the leg is maximized in the gait cycle; and adjusting a timing for outputting a torque to the leg based on the joint angle rate interval and the assistance power interval.

In some example embodiments, the method further includes measuring a joint angle of the leg; detecting a gait phase of the leg based on the joint angle; and calculating the torque based on the gait phase.

In some example embodiments, the detecting of the gait phase includes detecting the gait phase based on the joint angle and a particularly shaped adaptive oscillator (PSAO) model of the leg.

In some example embodiments, the leg of the user is a first leg of the user, and the detecting of the gait phase includes detecting the gait phase based on a joint angle of a second leg and a PSAO model of the second leg of the user.

In some example embodiments, the detecting of the gait phase includes detecting the gait phase based on the joint angle and a finite state machine (FSM) model of the leg.

In some example embodiments, the detecting the gait phase includes detecting gait phase based on the joint angle, a finite state machine (FSM) model of the leg, and an adaptive frequency oscillator (AFO) model of the leg.

In some example embodiments, the detecting the assistance power interval includes detecting the torque output to the leg; detecting the joint angle rate associated with the leg; calculating the assistance power based on the torque and the joint angle rate; and detecting the assistance power interval as an interval in which the assistance power is maximized in the gait cycle.

In some example embodiments, the detecting the joint angle rate includes detecting the joint angle rate using an angle rate sensor.

In some example embodiments, the detecting the joint angle rate includes detecting the joint angle rate based on a joint angle measured using an angle sensor.

In some example embodiments, the detecting the torque includes detecting the torque using a torque sensor.

In some example embodiments, the detecting the torque includes measuring, via a current sensor, a current flowing in a motor of the walking assistance; calculating an initial torque output by the motor based on the current; and calculating the torque based on the initial torque and a dynamic model of the walking assistance apparatus.

In some example embodiments, the detecting the joint angle rate interval includes detecting an interval in which the joint angle rate is maximized when the leg is in a stance state; and detecting an interval in which the joint angle rate is maximized when the leg is in a swing state.

In some example embodiments, the adjusting includes adjusting the timing such that the joint angle rate interval matches the assistance power interval, if the joint angle rate interval differs from the assistance power interval.

In some example embodiments, the adjusting includes adjusting the timing such that a difference between the joint angle rate interval and the assistance power interval is equal to a predefined offset.

In some example embodiments, the leg of the user is a first leg of the user, and the method further includes detecting a joint angle rate interval in which a joint angle rate of a second leg of the user wearing the walking assistance apparatus is maximized in a gait cycle of the second leg, wherein the adjusting adjusts the timing based on the joint angle rate interval of the first leg, the assistance power interval, and the joint angle rate interval of the second leg.

Some example embodiments relate to a torque output timing adjustment apparatus.

In some example embodiments, the apparatus includes a sensor configured to measure a joint angle rate of a leg of a user wearing a walking assistance apparatus; and a processor configured to, detect a joint angle rate interval in which the joint angle rate of the leg is maximized in a gait cycle of the leg, detect an assistance power interval in which an assistance power applied from the walking assistance apparatus to the leg is maximized in the gait cycle, and adjust a timing for outputting a torque to the leg based on the joint angle rate interval and the assistance power interval.

In some example embodiments, the sensor is configured to measure a joint angle of the leg, and the processor is configured to, detect a gait phase of the one based on the joint angle, and calculate the torque based on the gait phase.

In some example embodiments, the processor is configured to, detect the torque output to the leg, detect the joint angle rate of the leg, calculate the assistance power based on the torque and the joint angle rate, and detect the assistance power interval as an interval in which the assistance power is maximized in the gait cycle.

Some example embodiments relate to a method of adjusting a torque output timing of a torque output by a walking assistance apparatus to a leg of a user.

In some example embodiments, the method includes detecting a joint angle rate interval in which a joint angle rate of the leg of the user is maximized in a gait cycle of the one leg; detecting a torque interval in which a torque applied from the walking assistance apparatus to the leg is maximized in the gait cycle; and adjusting a timing for outputting the torque to the leg based on the joint angle rate interval and the torque interval.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which.

DETAILED DESCRIPTION

Figure 1:
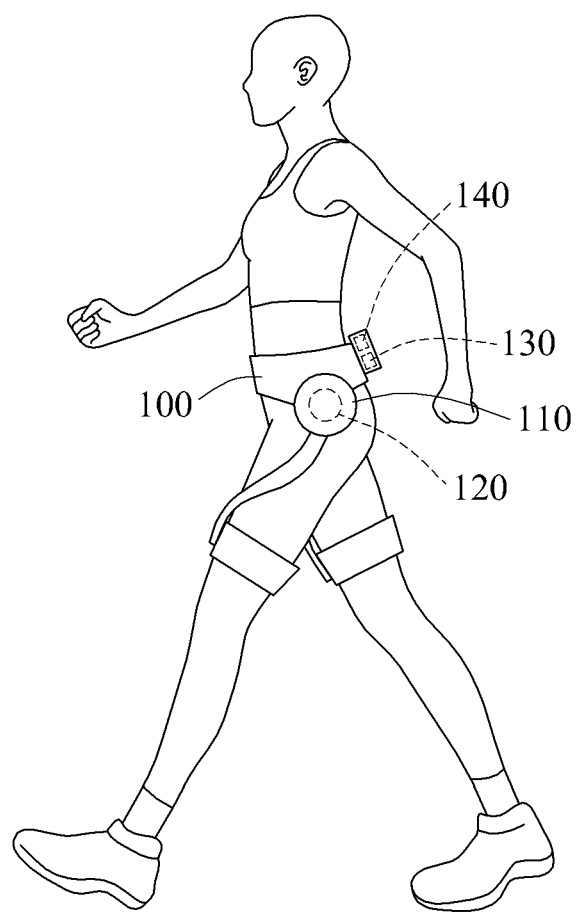
FIGS. 1 and 2 illustrate examples of a walking assistance apparatus.

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of embodiments, detailed description of well-known related structures or functions will be omitted when it is deemed that such description will cause ambiguous interpretation of the present disclosure.

It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

In addition, terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected", "coupled", or "joined" to another component, a third component may be "connected", "coupled", and "joined" between the first and second components, although the first component may be directly connected, coupled or joined to the second component.

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as one computer processing device; however, one skilled in the art will appreciate that a hardware device may include multiple processing elements and multiple types of processing elements. For example, a hardware device may include multiple processors or a processor and a controller. In addition, other processing configurations are possible, such as parallel processors.

Various example embodiments will now be described more fully with reference to the accompanying drawings in which some example embodiments are shown. In the drawings, the thicknesses of layers and regions are exaggerated for clarity.

<Outline of Walking Assistance Apparatus>

Figure 2:
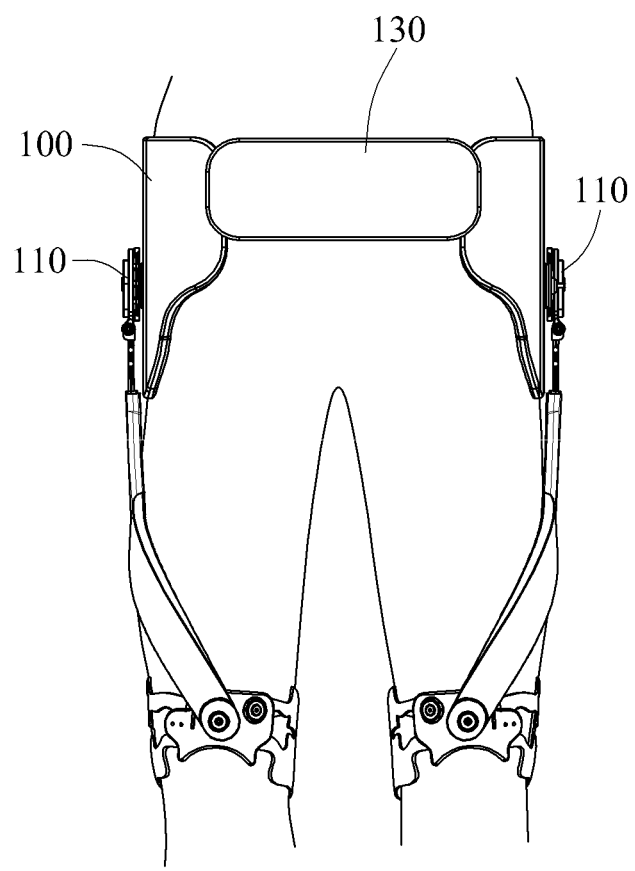

FIGS. 1 and 2 illustrate examples of a walking assistance apparatus 100.

Referring to FIG. 1, the walking assistance apparatus 100 may be configured to assist a gait of a user. The walking assistance apparatus 100 may be, for example, a wearable device.

Although FIG. 1 illustrates the walking assistance apparatus 100 provided as, for example, a hip-type walking assistance apparatus, a type of the walking assistance apparatus 100 is not limited thereto. The walking assistance apparatus 100 may be applicable to, for example, a walking assistance apparatus that supports an entire pelvic limb, a walking assistance apparatus that supports a portion of a pelvic limb, and the like. The walking assistance apparatus that supports a portion of a pelvic limb may be applicable to, for example, a walking assistance apparatus that supports up to a knee, and a walking assistance apparatus that supports up to an ankle.

Although, with reference to FIG. 1, the following descriptions are provided based on the hip-type walking assistance apparatus as an example, a type of the walking assistance apparatus is not limited thereto. Thus, this disclosure may be applicable to any apparatus configured to assist a gait of a user.

In an example, the walking assistance apparatus 100 may include a driver 110, a sensor 120, an inertial measurement unit (IMU) 130, and a controller 140.

The driver 110 may be disposed on each of a left hip portion and a right hip portion of a user to drive both hip joints of the user.

The driver 110 may include a motor (not shown) to generate a rotational torque.

The sensor 120 may measure both hip joint angle information of the user while the user is walking. The both hip joint angle information may include at least one of angles of both hip joints, a difference in the angles of the hip joints, and moving directions of the hip joints. For example, the sensor 120 may be included in the driver 110.

In an example, the sensor 120 may include at least one potentiometer. A potentiometer may be configured to sense R-axial and L-axial joint angle rates and R-axial and L-axial joint angles based on a gait motion of the user.

The IMU sensor 130 may measure acceleration information and posture information while the user is walking. For example, the IMU sensor 130 may sense X-axial, Y-axial, and Z-axial angle rates and X-axial, Y-axial, and Z-axial accelerations based on the gait motion of the user.

The walking assistance apparatus 100 may detect a landing time of a foot of the user based on the acceleration information measured by the IMU sensor 130. A pressure sensor (not shown) may be located on a sole of the user to detect the landing time of the foot of the user.

The walking assistance apparatus 100 may also include a sensor, for example, an electromyogram (EMG) sensor configured to sense a change in a biosignal or an amount of exercise of the user based on the gait motion of the user as well as the sensor 120 and the IMU sensor 130.

The controller 140 may include a communication device to communicate with an external device through the communication device.

The controller 140 may control the driver 110 to output an assistance power for assisting the user to walk. As an example, a hip-type walking assistance apparatus may include two drivers disposed on, for example, a left hip portion and a right hip portion. The controller 140 may output a control signal to control the driver 110 to generate a torque. Based on the control signal output from the controller 140, the driver 140 may generate the torque. The assistance torque may be provided to the user based on the torque.

Since an individual has a unique gait feature, a wearability of a walking assistance apparatus may decrease if the walking assistance apparatus uniformly output a torque at the same timing. Thus, in one or more example embodiments, the walking assistance apparatus 100 may adjust a timing of the output torque to increase the wearability. In response to the adjusted timing of the output torque, a timing of an assistance power output based on the torque and a joint angle rate may be adjusted. Due to the walking assistance apparatus 100 outputting the assistance power at a desired point in time, a user may wear the walking assistance apparatus 100 with an increased comfort.

A torque output timing adjustment method will be also described as an example with reference to FIGS. 3 through 21.

<Torque Output Timing Adjustment Apparatus>

Figure 3:
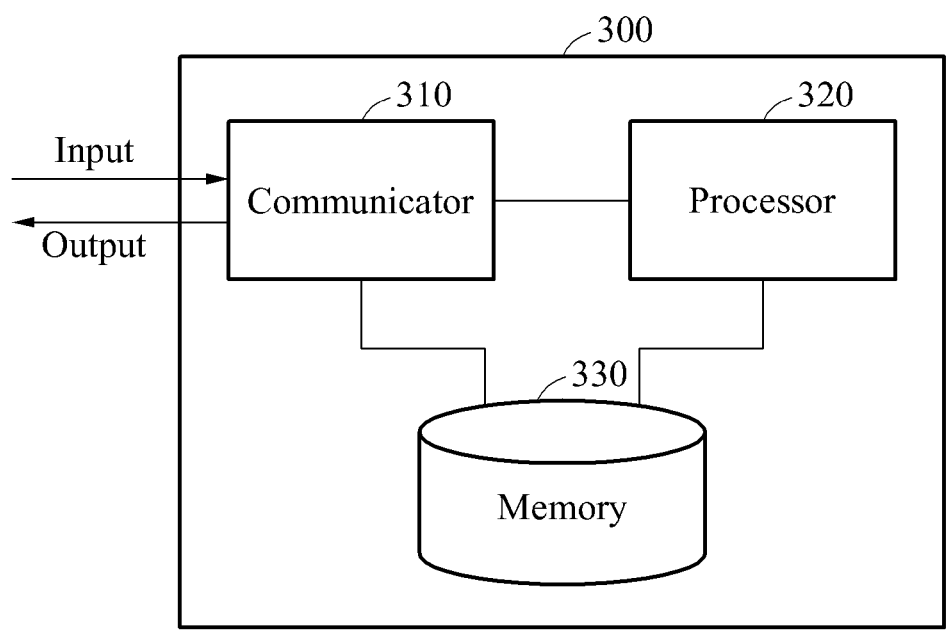
FIG. 3 illustrates an example of a torque output timing adjustment apparatus.

FIG. 3 illustrates a torque output timing adjustment apparatus 300.

The torque output timing adjustment apparatus 300 may include a communicator 310, a processor 320, and a memory 330.

The communicator 310 may include transmitters and/or receivers. The transmitters may include hardware and any necessary software for transmitting signals including, for example, data signals and/or control signals to the driver 110. The receivers may include hardware and any necessary software for receiving signals including, for example, data signals and/or control signals from one or more sensors 120, 130.

The communicator 310 may perform a data exchange or an information exchange with devices of the walking assistance apparatus 100 or external devices.

The processor 320 may be implemented by at least one semiconductor chip disposed on a printed circuit board. The processor 320 may be an arithmetic logic unit, a digital signal processor, a microcomputer, a field programmable array, a programmable logic unit, a microprocessor or any other device capable of responding to and executing instructions in a defined manner.

The processor 320 may be programmed with instructions that configure the processor 320 into a special purpose computer to perform the operations illustrated in one or more of FIGS. 4 and 21 and their associated sub-routines, discussed below, such that the processor 320 is configured to adjust a timing for outputting an assistance torque to the user based on a joint angle rate and a timing when one of an assistance power and torque is a local maximum (or, alternatively, near maximum).

The processor 320 may process data received by the communicator 310 and data stored in the memory 330. In an example, the processor 320 may be included in the controller 140.

The memory 330 may be a non-volatile memory, a volatile memory, a hard disk, an optical disk, and a combination of two or more of the above-mentioned devices. The memory may be a non-transitory computer readable medium. The non-transitory computer-readable media may also be a distributed network, so that the program instructions are stored and executed in a distributed fashion. The non-volatile memory may be a Read Only Memory (ROM), a Programmable Read Only Memory (PROM), an Erasable Programmable Read Only Memory (EPROM), or a flash memory. The volatile memory may be a Random Access Memory (RAM).

The memory 330 may store the data received by the communicator 310 and data processed by the processor 320.

The communicator 310, the processor 320, and the memory 330 will be also described as an example with reference to FIGS. 4 through 21.

Figure 4:
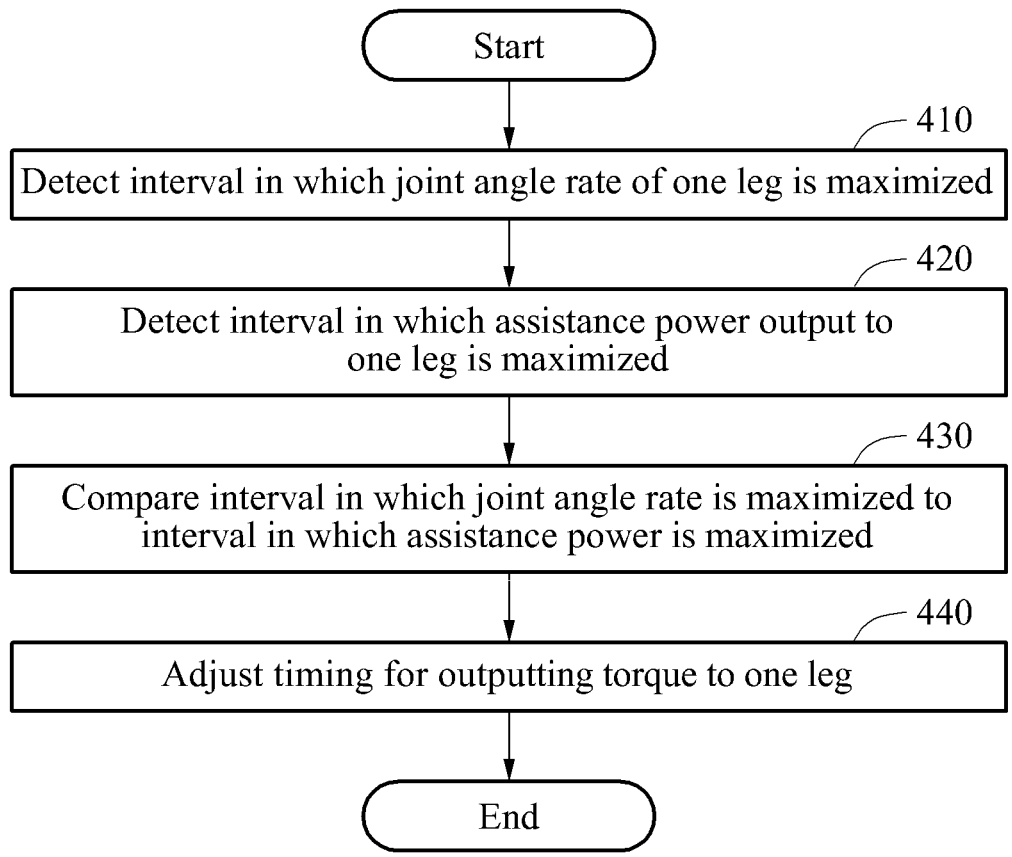
FIG. 4 illustrates an example of a torque output timing adjustment method.

FIG. 4 illustrates an example of a torque output timing adjustment method.

In operation 410, the processor 320 may detect an interval in which a joint angle rate of one leg is maximized. The one leg may be either a left leg or a right leg of a user. The joint angle rate may be of, for example, at least one of a hip joint, a knee joint, and an ankle joint. As an example, the processor 320 may detect the interval in which the joint angle rate is maximized based on a trajectory of a joint angle rate of the one leg measured in a previous gait cycle. The interval in which the joint angle rate is maximized may be, for example, a peak point corresponding to a maximum joint angle rate. In terms of the gait cycle, one cycle may be defined as a period of time between an instant at which a first leg touches a ground and an instant at which the first leg re-touches the ground.

Figure 6:
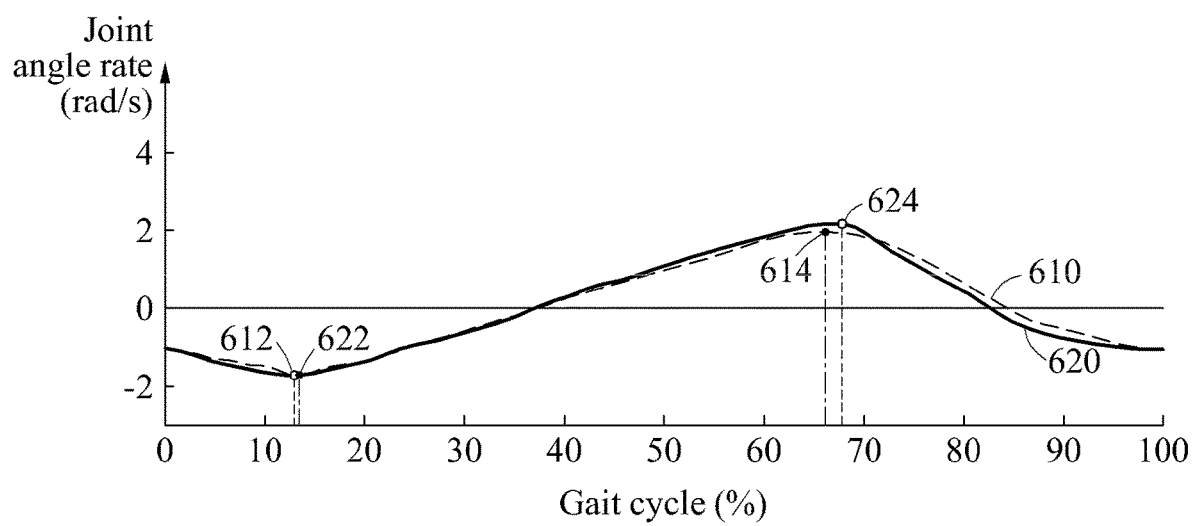
FIG. 6 illustrates an example of a joint angle rate of a normal gait.

The interval in which the joint angle rate is maximized will be also described as an example with reference to FIG. 6.

In operation 420, the processor 320 may detect an interval in which an assistance power output to the one leg is maximized. The output assistance power may be calculated based on an output torque and the joint angle rate. The assistance power may be, for example, an assistance work ratio. The interval in which the output assistance power is maximized may be, for example, a peak point corresponding to a maximum output assistance power.

The output torque, the output assistance power, and a method of calculating the output assistance power will be described as an example with reference to FIGS. 7 through 9.

In operation 430, the processor 320 may compare the interval in which the joint angle rate is maximized to the interval in which the output assistance power is maximized. As an example, the processor 320 may compare a first gait phase of the interval in which the joint angle rate is maximized to a second gait phase of the interval in which the output assistance power is maximized. The gait phase is a phase within in a gait cycle, indicates a progress of the walking within one gait cycle. Percent gait cycle (% GC) is a commonly used unit to denote gait phase. For examples, heel strikes the ground on 0% gait cycle, a toe of the opposite foot is off the ground around 60% gait cycle. The PSAO detected the current gait phase as 0.55 or 55% GC. The processor 320 may compare the first gait phase to the second gait phase and calculate a difference between the first gait phase and the second gait phase.

In operation 440, the processor 320 may adjust a timing for outputting a torque to the one leg based on a result of the comparing. In this disclosure, the timing for outputting a torque may also be referred to as, for example, a torque output timing. As an example, when the first gait phase does not match the second gait phase, the processor 320 may adjust the torque output timing such that the first gait phase matches the second gait phase. As another example, the processor 320 may adjust the torque output timing such that a difference between the first gait phase and the second gait phase corresponds to a desired difference or predefined offset.

Figure 15:
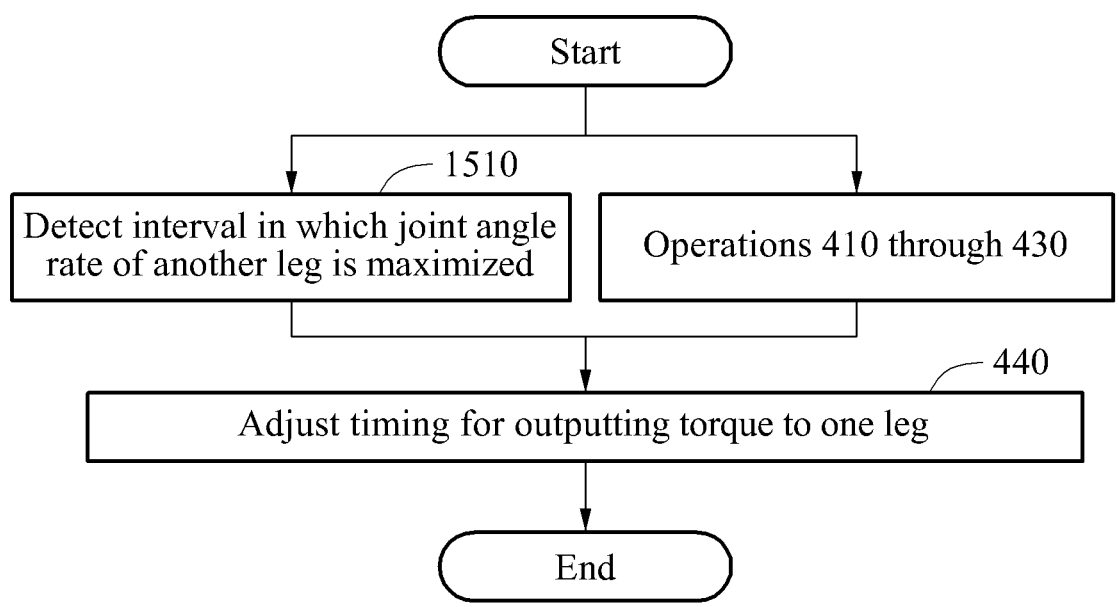
FIG. 15 illustrates an example of a method of adjusting a timing for outputting a torque to one leg based on a joint angle rate of another leg.

A method of adjusting the torque output timing will be also described as an example with reference to FIG. 15.

A joint angle, a joint angle rate, an output torque, and an output assistance power of a normal gait will be described as an example with reference to FIGS. 5 through 8. The normal gait may indicate that the left leg and the right leg move symmetrically while the user is walking. In the normal gait, a period of the gait cycle of the left leg may be similar to or the same as a period of the gait cycle of the right leg. In the drawings, the joint angle, the joint angle rate, the output torque, and the output assistance power may be related to the previous gait cycle and used to adjust a torque output timing of a current gait cycle. The previous gait cycle may be, for example, an average value of a plurality of gait cycles.

Figure 5:
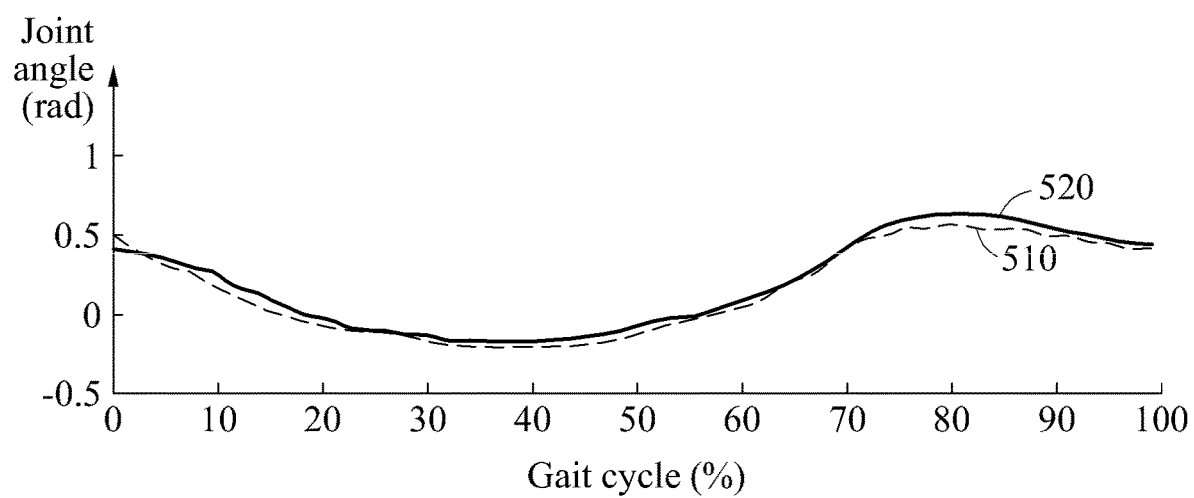
FIG. 5 illustrates an example of a joint angle of a normal gait.

FIG. 5 illustrates an example of a joint angle of a normal gait.

FIG. 5 illustrates a trajectory 510 of a joint angle of a left leg and a trajectory 520 of a joint angle of a right leg based on the same gait cycle. An instant at which a leg touches a ground may correspond to a gait cycle 0%, and an instant at which the leg re-touches the ground may correspond to a gait cycle 100%.

The trajectory 510 and the trajectory 520 may indicate similar joint angles or the same joint angle with respect to the same gait phase.

FIG. 6 illustrates an example of a joint angle rate of a normal gait.

FIG. 6 illustrates a trajectory 610 of a joint angle rate of a left leg and a trajectory 620 of a joint angle rate of a right leg based on the same gait cycle. When the trajectory 510 is similar or identical to the trajectory 520, the trajectory 610 may also be similar or identical to the trajectory 620.

From each of the trajectory 610 and the trajectory 620, the processor 320 may detect an interval in which a joint angle rate is maximized and a gait phase corresponding to the interval. As an example, the interval in which the joint angle rate is maximized may be a peak point corresponding to a maximum joint angle rate, and the gait phase to the interval may be a preset gait cycle of the peak point. As another example, the interval in which the joint angle is maximized may be an interval corresponding to at least a preset value, and the gait phase corresponding to the interval may be a preset gait cycle of a middle point in the interval.

The processor 320 may detect the interval in which the joint angle rate is maximized based on a state of a leg. The processor 320 may determine the state of the leg based on a joint angle of the leg using a finite state machine (FSM). The processor 320 may detect an interval 612 or 622 in which a joint angle rate is maximized while one leg is in a stance state. Also, the processor 320 may detect an interval 614 or 624 in which the joint angle rate is maximized while the one leg is in a swing state.

When the trajectory 610 is similar or identical to the trajectory 620, gait phases of intervals detected from the trajectory 610 and the trajectory 620 may also be similar or identical to each other. For example, a difference between a timing of the interval 614 and a gait phase of the interval 624 may be 3% or less.

Figure 7:
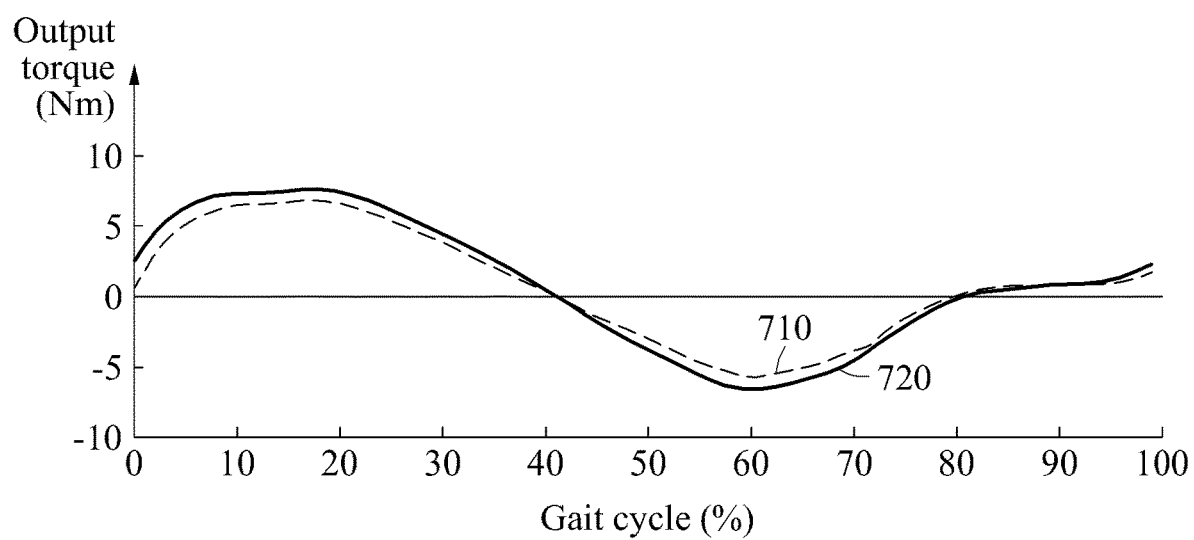
FIG. 7 illustrates an example of an output torque of a normal gait.

FIG. 7 illustrates an example of an output torque of a normal gait.

The processor 320 may acquire trajectories 710 and 720 of an output torque of a previous gait cycle for a left leg and a right leg, respectively. A torque output in a preset gait phase of a gait cycle may be calculated based on a joint angle measured in the preset gait phase. The torque may be calculated by the controller 140. Alternatively, the torque may be calculated by the processor 320. A method of calculating the output torque using the processor 320 will be described as an example with reference to FIGS. 11 through 14.

FIG. 7 illustrates the trajectory 710 of a left leg and the trajectory 720 of a right leg based on the same gait cycle. When the trajectory 510 and the trajectory 520 of FIG. 5 are similar or identical to each other, the trajectory 710 may be similar or identical to the trajectory 720.

Figure 8:
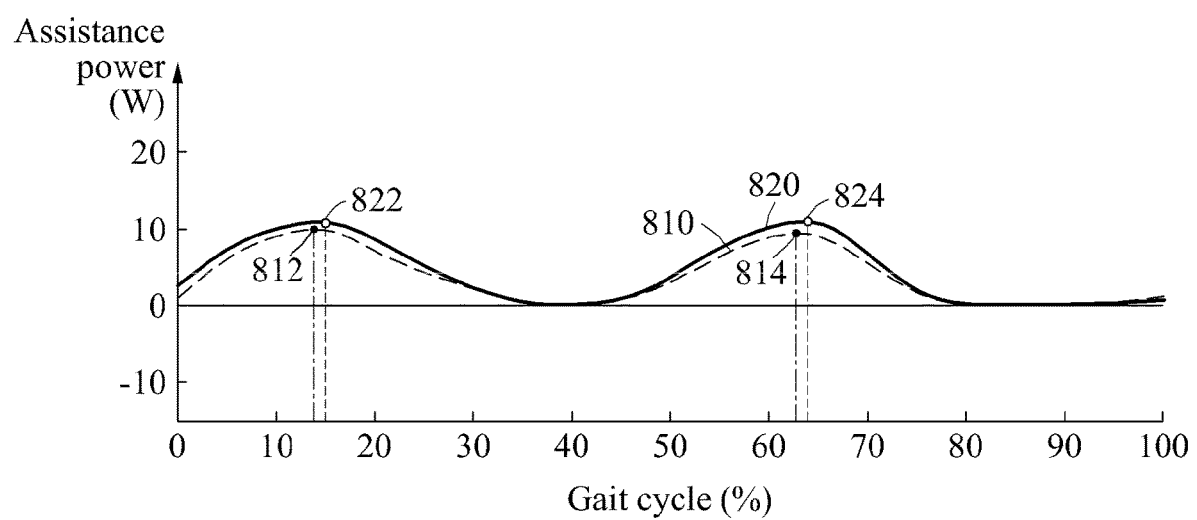
FIG. 8 illustrates an example of an output assistance power of a normal gait.

FIG. 8 illustrates an example of an output assistance power of a normal gait.

When the trajectory 510 and the trajectory 520 of FIG. 5 are similar or identical to each other, a trajectory 810 of an output assistance power of a left leg may be similar or identical to a trajectory 820 of an output assistance power of a right leg.

The processor 320 may calculate an output assistance power based on a joint angle rate and an output torque. For example, the processor 320 may calculate the output assistance power by multiplying the joint angle rate by the output torque. When a torque is output in a moving direction of a leg, an intensity of the assistance power may have a positive value. Conversely, when the torque is output in a reverse direction of the moving direction, the intensity of the assistance power may have a negative value.

When a gait phase of an interval in which a joint angle rate of the left leg is maximized, for example, the interval 612 and the interval 614 outpaces a gait phase of an interval in which a joint angle rate of the right leg is maximized, for example, the interval 622 and the interval 624, a gait phase of an interval in which the output assistance power of the left leg is maximized, for example, an interval 812 and an interval 814 may outpace a gait phase of an interval in which the output assistance power of the right leg is maximized, for example, an interval 822 and an interval 824.

When a maximum assistance power is provided to the left leg of the user at a point in time corresponding to a maximum joint angle rate of the left leg, a comfort that the user may experience may be increased. For the increased comfort of the user, in one or more example embodiments, the processor 320 may adjust a torque output timing to provide an assistance power at a desired time.

Figure 9:
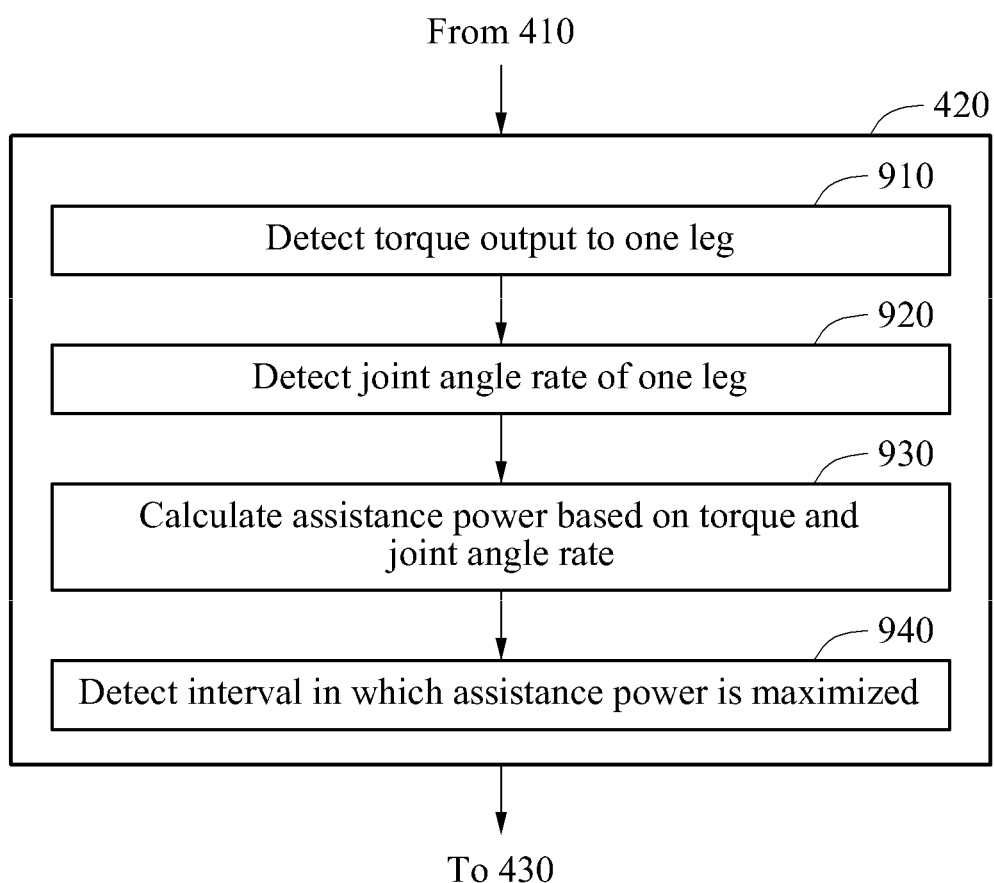
FIG. 9 illustrates an example of a method of detecting an interval in which an output assistance power is maximized.

FIG. 9 illustrates an example of a method of detecting an interval in which an output assistance power is maximized.

Operation 420 may include operations 910 through 940.

In operation 910, the processor 320 may detect a torque output to one leg. The processor 320 may detect the torque output to the one leg from at least one previous gait cycle. For example, the processor 320 may detect a trajectory of a torque output based on a gait cycle.

The processor 320 may calculate a torque output by a motor using a torque sensor. The processor 320 may also detect the torque based on a current value of the motor. A method of detecting the torque based on the current value of the motor will be described as an example with reference to FIG. 10.

In operation 920, the processor 320 may detect a joint angle rate of the one leg. The processor 320 may detect the joint angle rate of the one leg using an angle rate sensor. The processor 320 may detect the joint angle rate from at least one previous gait cycle. For example, the processor 320 may detect a trajectory of the joint angle rate of the one leg output based on the gait cycle.

FIG. 9 illustrates that operation 910 is performed prior to operation 920 for ease and convenience of description and thus, operation 920 may also be performed prior to operation 910.

In operation 930, the processor 320 may calculate an output assistance power based on the output torque and the joint angle rate. The processor 320 may calculate the output assistance power by multiplying the torque by the joint angle rate. For example, the processor 320 may calculate a trajectory of the output assistance torque corresponding to the gait cycle based on the trajectory of the torque and the joint angle rate.

In operation 940, the processor 320 may detect an interval in which the output assistance power is maximized. For example, the processor 320 may detect the interval in which the output assistance power is maximized based on the trajectory of the output assistance power.

Figure 10:
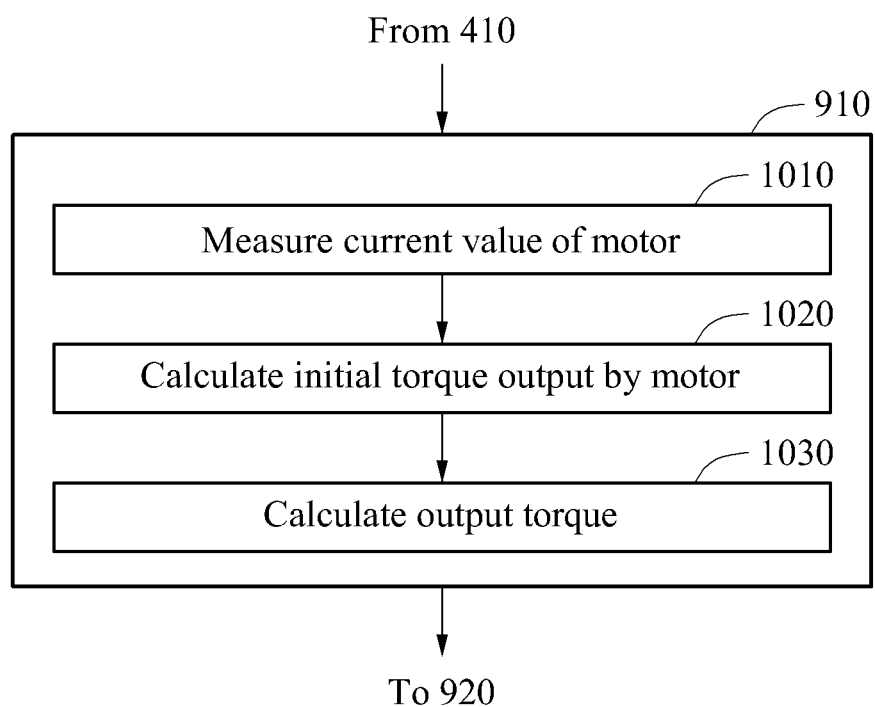
FIG. 10 illustrates an example of a method of detecting a torque output to one leg.

FIG. 10 illustrates an example of a method of detecting a torque output to one leg.

Operation 910 may include operations 1010 through 1030.

In operation 1010, the processor 320 may measure a current value of a motor using a current sensor configured to measure a current value.

In operation 1020, the processor 320 may calculate an initial torque output by the motor based on the measured current value.

In operation 1030, the processor 320 may calculate an output torque based on the initial torque and a dynamic model of a walking assistance apparatus. The dynamic model may be, for example, a model that the initial torque is delivered to the user as the output torque.

Figure 11:
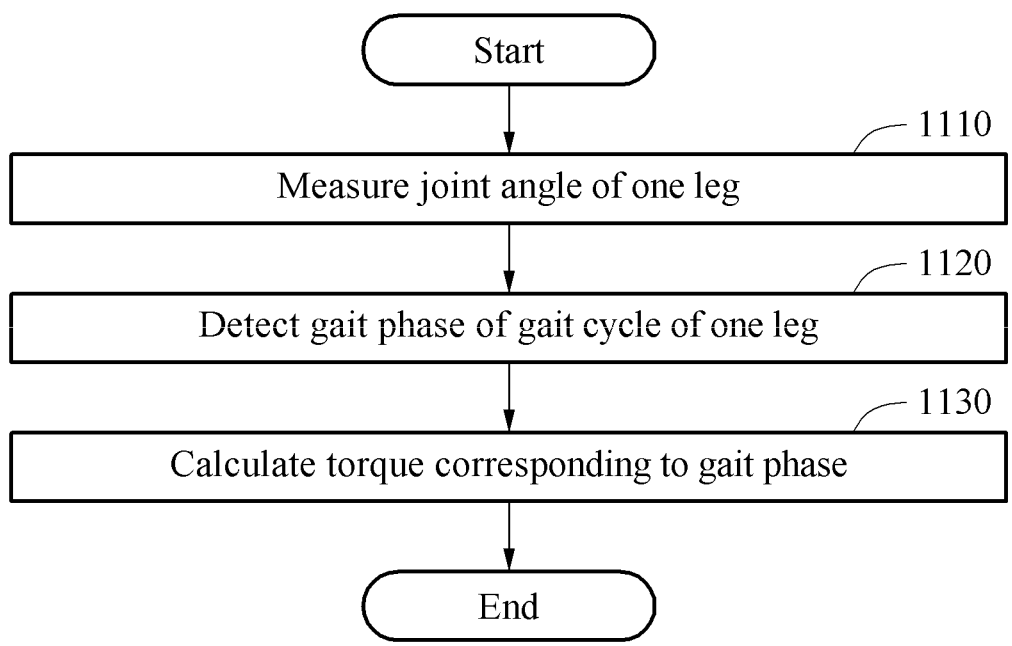
FIG. 11 illustrates an example of a method of calculating a torque corresponding to a gait phase.

FIG. 11 illustrates an example of a method of calculating a torque corresponding to a gait phase of a gait cycle.

A torque output timing adjustment method may further include operations 1110 through 1130. Operations 1110 through 1130 may be performed before operation 440 is performed. Operations 410 through 430 may be performed on a previous gait cycle, and operation 440 may be performed on a current gait cycle. Operations 1110 through 1130 may be performed on the current gait cycle.

In operation 1110, the processor 320 may measure a joint angle of one leg. The processor 320 may measure the joint angle of the one leg using an angle sensor.

In operation 1120, the processor 320 may detect a gait phase of a gait cycle of the one leg based on the measured joint angle.

In an example, the processor 320 may detect the gait phase of the gait cycle based on the measured joint angle of the one leg and a particularly shaped adaptive oscillator (PSAO) of the one leg. Additionally, the processor 320 may detect the gait phase of the gait cycle based on a joint angle of another leg of a user wearing the walking assistance apparatus 100 and a PSAO of the other leg. A method of detecting the gait phase of the gait cycle based on the PSAO will be described as an example with reference to FIG. 12.

In another example, the processor 320 may detect the gait phase of the gait cycle based on the measured joint angle of the one leg and an FSM. The processor 320 may also detect the gait phase of the gait cycle based on the measured joint angle of the one leg and the FSM and an adaptive frequency oscillator (AFO). A method of detecting the gait phase of the gait cycle based on the FSM and the AFO will be described as an example with reference to FIGS. 13 through 15.

In operation 1130, the processor 320 may calculate a torque corresponding to the detected gait phase. For example, the processor 320 may calculate the torque based on a table mapped to the gait phase of the gait cycle. The processor 320 may adjust the table using a torque output in a previous gait cycle.

The torque calculated based on the gait phase may be output at a set output timing. The set output timing may be, for example, a timing adjusted in operation 440.

Figure 12:
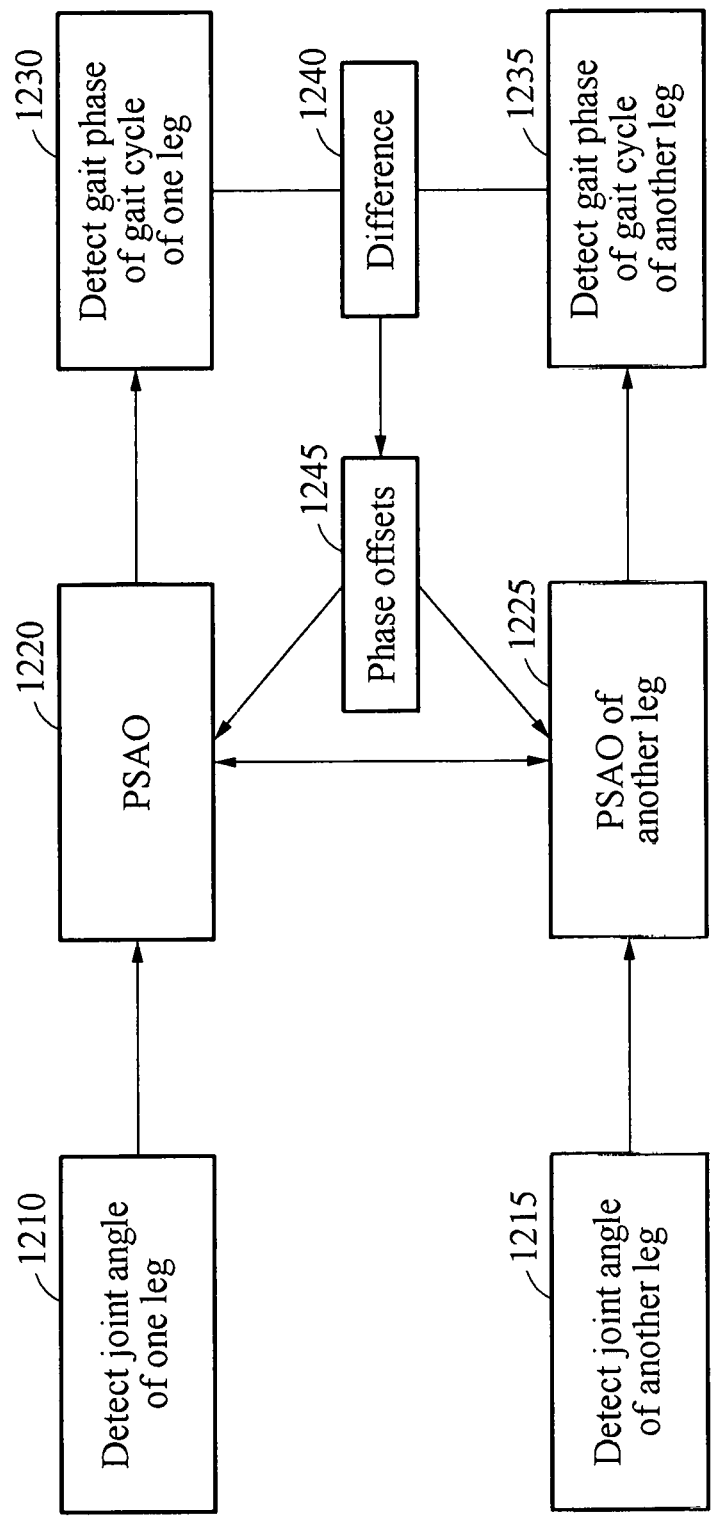
FIG. 12 illustrates an example of a method of detecting a gait phase based on a particularly shaped adaptive oscillator (PSAO)

FIG. 12 illustrates an example of a method of detecting a gait phase of a gait cycle based on a PSAO.

Operation 1110 may include operations 1210 and 1215, and operation 1120 may include operations 1220 through 1240.

In operation 1210, the processor 320 may detect a joint angle of one leg.

In operation 1215, the processor 320 may detect a joint angle of another leg.

In operation 1220, the processor 320 may calculate a gait frequency of the one leg using a PSAO.

The PSAO may include a plurality of oscillators, each having an offset, a fundamental frequency, and/or a frequency modulated from the fundamental frequency. The plurality of oscillators may have respective phases and amplitudes. The frequency modulated from the fundamental frequency may be an integer multiple frequency of the fundamental frequency.

In detail, the PSAO may obtain angles of the plurality of oscillators by applying a reference trajectory, the phases, and the amplitudes to the plurality of oscillators, each having the fundamental frequency and a frequency corresponding to an integer multiple of the fundamental frequency.

The PSAO may generate an overlapping angle by overlapping the angles obtained from the plurality of oscillators. The PSAO may generate an overlapping angle trajectory by combining generated overlapping angles in an order of a gait cycle. The PSAO may iteratively correct the fundamental frequency, the offset, the phase, and the amplitude of each of the plurality of oscillators to minimize an error between the overlapping angle and the measured joint angle.

By iteratively performing the correction, the processor 320 may approximate the overlapping angle trajectory to a trajectory of the measured joint angle. The fundamental frequency, the offset, and the amplitude of each of the plurality of oscillators may converge to a desired value to correspond to the trajectory of the measured joint angle.

When the generated overlapping angle trajectory corresponds to the trajectory of the measured joint angle, the fundamental frequency of the PSAO may correspond to the gait frequency. A phase of an oscillator having the fundamental frequency may correspond to a current gait phase.

Hereinafter, a method of correcting a fundamental frequency, an offset, a phase, and an amplitude of each of a plurality of oscillators for the aforementioned PSAO to periodically correspond to a trajectory of a measured joint angle, and a method of calculating a gait phase will be described using the following equations.

$$\theta_p(n) = \alpha_0 + \sum_{i=1} \alpha_i(n) f(\varphi_i(n)) \qquad \text{[Equation 1]}$$

The processor 320 may use Equation 1 to calculate an overlapping angle.

In Equation 1, i denotes a plurality of oscillators of a PSAO, n denotes an index of a measurement and correction cycle of a joint angle, $\theta_p$ denotes an overlapping angle, $\alpha_o$ denotes an offset of the overlapping angle, $\alpha_i$ denotes an amplitude of an $i^{th}$ oscillator, $f(\varphi)$ denotes a function of a reference trajectory, and $\varphi_i$ denotes a phase of the $i^{th}$ oscillator.

$$\varepsilon(n) = \theta_h(n) - \theta_p(n) \qquad \text{[Equation 2]}$$

The processor 320 may use Equation 2 to calculate an error value. The error value may be a difference value between a measured joint angle and the overlapping angle calculated using Equation 1.

In Equation 2, $\varepsilon$ denotes an error value, and $\theta_h$ denotes a measured joint angle.

$$f'(\varphi) = \frac{\partial f}{\partial \varphi}(\varphi) \qquad \text{[Equation 3]}$$

The processor 320 may calculate a variation in a joint angle reference trajectory of an oscillator of a PSAO using Equation 3.

$$\alpha_i(n+1) = \max\left\{0, \alpha_i(n) + T_g \frac{k_a}{i} ef(\varphi_i(n))\right\} \qquad \text{[Equation 4]}$$

The processor 320 may use Equation 4 to correct an amplitude of an oscillator having an i-fold frequency of a fundamental frequency, among a plurality of oscillators of a PSAO.

In Equation 4, an amplitude correction quantity of an oscillator may be calculated by multiplying an amplitude correction gain, an error value, and a resulting value obtained by applying a phase of an $i^{th}$ oscillator to a function of a reference trajectory, and dividing a resulting value of the multiplying by an index of the oscillator.

In Equation 4, a current amplitude correction value may be calculated by multiplying the amplitude correction quantity by a correction iteration period Ts, and adding a previous amplitude correction value to a resulting value of the multiplying.

In Equation 4, an offset may be set such that the current amplitude correction value is greater than or equal to "0". An error value between the measured joint angle and the overlapping angle may be reduced through Equation 4.

In Equation 4, $k_a$ denotes an amplitude correction gain, Ts denotes a measurement and correction iteration period of a joint angle. The sampling period may be within a range of about 1 to 10 milliseconds (ms).

$$\varphi_i(n+1) = \varphi_i(n) + T_g\left(i\omega(n) + k_\varphi \frac{\varepsilon}{\sum \alpha_i(n)} f'(\varphi_i(n))\right). \qquad \text{[Equation 5]}$$

The processor 320 may use Equation 5 to calculate a phase of an oscillator having an i-fold frequency of a fundamental frequency, among a plurality of oscillators of a PSAO.

The $i^{th}$ oscillator may have the i-fold frequency of the fundamental frequency. A phase increment may vary due to a value obtained by multiplying an error value by a variation in a reference trajectory. Thus, an error value between a trajectory of a measured joint angle and an overlapping angle trajectory may decrease.

To correct a phase, a first value may be calculated by multiplying an index of an oscillator by a fundamental frequency of the PSAO, and a second value may be calculated by multiplying a phase correction gain, an error, and a resulting value obtained by applying a phase of the oscillator to a function with respect to a variation in a reference trajectory, and dividing a resulting value of the multiplying by a sum of amplitudes of the plurality of oscillators. A phase correction value of the $i^{th}$ oscillator may be calculated by adding the first value and the second value. By multiplying a correction cycle period by the calculated correction value, and adding a phase corrected at a previous sampling time to a resulting value of the multiplying, a currently corrected phase of the $i^{th}$ oscillator may be calculated.

In Equation 5, $k_\varphi$ denotes a phase correction gain, and $\omega$ denotes a fundamental frequency of a PSAO.

$$\omega(n+1) = \omega(n) + \qquad\qquad\qquad\qquad \text{[Equation 6]}$$
$$T_g\left(k_\omega \frac{\varepsilon}{\sum \alpha_i} f'(\varphi_1) + \sum k_e e^{-\frac{(\omega_{ext}-\omega)^2}{2}}(\omega_{ext}-\omega)\right)$$

The processor 320 may use Equation 6 to correct a fundamental frequency of a PSAO.

In Equation 6, a third value may be calculated by multiplying a frequency correction gain, an error value, and a resulting value obtained by applying a phase of a first oscillator to a function with respect to a variation in a reference trajectory, and dividing a resulting value of the multiplying by a sum of amplitudes of a plurality of oscillators.

In Equation 6, a fourth value may be obtained by adding, with respect to all joints excluding the joint calculated in Equation 6, values obtained by multiplying a coupling frequency gain, a natural exponential value of a value obtained by multiplying $-\frac{1}{2}$ by a square of a difference between a frequency of a joint angle trajectory measured by another PSAO in another aspect and a fundamental frequency of the present PSAO, and a difference between the frequency of the joint angle trajectory measured in the other aspect and the fundamental frequency.

For example, the present PSAO may measure a frequency of an angle trajectory of a right hip joint, and the other PSAO may measure a frequency of an angle trajectory of a left hip joint.

The third value of Equation 6 may be a value to correct the fundamental frequency so that the fundamental frequency of the PSAO may correspond to a frequency of the trajectory of the measured joint angle.

In general, an estimated frequency of a left joint angle trajectory may coincide with an estimated frequency of a right joint angle trajectory. When the estimated frequencies differs from one another, the fourth value may be a value to correct the fundamental frequency to match the different frequencies.

In detail, a natural exponential portion of the fourth value may converge to "0" when the difference between the two frequencies is great. Thus, coupling between the two frequencies may be blocked. The natural exponential portion of the fourth value may induce the two frequencies to be identical to each other when the difference between the two frequencies is modest.

A sum of the third value and the fourth value may be a correction quantity of the fundamental frequency of the PSAO. By multiplying the sum of the third value and the fourth value by the correction period, and adding a previous correction fundamental frequency to a resulting value of the multiplying, a current correction fundamental frequency may be calculated.

In Equation 6, $k_\omega$ denotes a frequency correction gain, $k_c$ denotes a coupling frequency gain, and $\omega_{ext}$ denotes a frequency of a joint angle trajectory measured by another PSAO in another aspect.

$$\alpha_o(n+1) = \alpha_o(n) + T_g k_o \varepsilon \qquad\qquad \text{[Equation 7]}$$

The processor 320 may use Equation 7 to correct an offset of an overlapping angle of a PSAO.

Equation 7 may reduce a calculation error resulting from an offset by correcting the offset of the overlapping angle of the PSAO to correspond to an offset of a measured joint angle.

In Equation 7, $k_o$ denotes an offset correction gain. Through the aforementioned equations, the PSAO may match the overlapping angle trajectory and the trajectory of the measured joint angle by continuously calculating, during a gait duration, an overlapping angle to correspond to the measured joint angle.

Using Equations 1 through 7, the processor 320 may calculate a gait frequency.

In operation 1230, the processor 320 may detect a gait phase of the gait cycle of the one leg based on the gait frequency.

The processor 320 may acquire the gait phase of the gait cycle using a phase compensated adaptive oscillator (PCAO).

In an example, the PCAO may be a signal processing module that receives a measured joint angle as an input, and outputs a current gait cycle. In another example, the PCAO may be a subordinate concept of a PSAO, and may substitute a reference trajectory of the PSAO with a sinusoidal wave.

The processor 320 may include a PCAO module. In the following descriptions, descriptions of the PCAO may be construed as descriptions of the processor 320.

The PCAO may include a first adaptive oscillator AO-1, a second adaptive oscillator AO-2, and a gait cycle calculator. The first adaptive oscillator AO-1 may receive a measured joint angle as an input, and calculate a first overlapping angle trajectory by overlapping trigonometrical functions having a fundamental frequency and a frequency modulated from the fundamental frequency. The first adaptive oscillator AO-1 may calculate a first phase corresponding to a phase of a trigonometrical function having the fundamental frequency. The second adaptive oscillator AO-2 may apply a reference angle on a reference trajectory corresponding to a current gait cycle to the trigonometrical functions having the fundamental frequency and the frequency modulated from the fundamental frequency based on the current gait cycle calculated by the gait cycle calculator. The second adaptive oscillator AO-2 may calculate a second overlapping angle trajectory by overlapping the trigonometrical functions to which the reference angle is applied. The second adaptive oscillator AO-2 may calculate a second phase corresponding to a phase of a trigonometrical function having the fundamental frequency.

The first adaptive oscillator AO-1 of the PCAO is a module that calculates only a phase corresponding to an angle of a currently measured joint. Thus, the first adaptive oscillator AO-1 may not compensate for the first overlapping angle trajectory with the second overlapping angle trajectory calculated based on the reference trajectory while the user is walking. To compensate for the first overlapping angle trajectory with the second overlapping angle trajectory, the second adaptive oscillator AO-2 of the PCAO may be additionally included.

The gait phase calculator may calculate a current gait phase by reflecting a phase difference between the first phase and the second phase based on the first phase calculated by the first adaptive oscillator AO-1 and the second phase calculated by the second adaptive oscillator AO-2.

The first phase output from the first adaptive oscillator AO-1 may be a phase of the first overlapping angle trajectory overlapped by applying the measured joint angle to trigonometrical functions having a fundamental frequency of the first adaptive oscillator AO-1 and a frequency modulated from the fundamental frequency. The first phase may be a phase of a trigonometrical function having the fundamental frequency, among the trigonometrical functions constituting the phase of the first overlapping angle trajectory.

Since the first phase is not calculated under an assumption that an instant at which a heel of a foot touches the ground is the reference point in time, the first phase may not correspond to the gait cycle. To compensate for such a difference in the reference point in time, the gait phase calculator may determine the gait phase of the gait cycle by correcting the first phase. The first phase may be corrected by calculating the second overlapping angle trajectory using the second adaptive oscillator AO-2, and comparing the second phase corresponding to the phase of the second overlapping angle trajectory to the first phase.

In an example, the second phase calculated by the second adaptive oscillator AO-2 based on the reference angle of the reference trajectory corresponding to the gait cycle may be a phase of the second overlapping angle trajectory calculated by overlapping trigonometrical functions having a fundamental frequency of the second adaptive oscillator AO-2 and a frequency modulated from the fundamental frequency. The second phase may be a phase of a trigonometrical function having the fundamental frequency, among the trigonometrical functions constituting the phase of the second overlapping angle trajectory.

The PCAO may calculate the gait phase of the gait cycle by compensating for the first phase based on a phase difference between the second phase and the first phase accumulated by the gait phase calculator.

The first adaptive oscillator AO-1 and the second adaptive oscillator AO-2 may be adaptive oscillator (AO) modules. Operations of the first adaptive oscillator AO-1 and the second adaptive oscillator AO-2 will be also described as an example using the following equations.

$$\theta_p(n) = \alpha_0 + \sum_{i=1} \alpha_i(n)\sin(\varphi_i(n)) \quad \text{[Equation 8]}$$

The processor 320 may use Equation 8 to calculate overlapping angles in the first adaptive oscillator AO-1 and the second adaptive oscillator AO-2.

An overlapping angle may be calculated by adding an offset to a sum of values obtained by multiplying values obtained by applying phases of a plurality of oscillators constituting a single AO to a sine function by amplitudes of the respective oscillators.

The PSAO may calculate an overlapping angle to correspond to the measured joint angle, and continuously perform the calculation during a gait time, thereby approximating the overlapping angle to the trajectory of the measured joint angle.

In Equation 8, i denotes indices of a plurality of oscillators, n denotes an index of a measurement and correction cycle of a joint angle, $\theta_p$ denotes an overlapping angle, $\alpha_0$ denotes an offset of the overlapping angle, $\alpha_i$ denotes an amplitude of an $i^{th}$ oscillator, and $\varphi_i$ denotes a phase of the $i^{th}$ oscillator.

$$\varepsilon(n) = \theta_h(n) - \theta_p(n) \quad \text{[Equation 9]}$$

The processor 320 may use Equation 9 to calculate an error value in a single AO.

The error value may be a difference value between an input value of the AO and the overlapping angle calculated by Equation 8. An input value of the first adaptive oscillator AO-1 may be the measured joint angle, and an input value of the second adaptive oscillator AO-2 may be the reference angle corresponding to the current gait phase.

In Equation 9, ε denotes an error value, and $\theta_h$ denotes an input value of the AO.

$$\alpha_i(n+1) = \max\left\{0, \alpha_i(n) + T_g \frac{k_\alpha}{i} \varepsilon \sin(\varphi_i(n))\right\} \quad \text{[Equation 10]}$$

The processor 320 may use Equation 10 to correct amplitudes of oscillators having an i-fold frequency of a fundamental frequency, among a plurality of oscillators of a PCAO. In Equation 10, $k_\alpha$ denotes an amplitude correction gain, $T_s$ denotes a measurement and correction iteration period of a joint angle and a sample period. The sampling period may be within a range of about 1 to 10 ms.

An amplitude correction quantity of an oscillator may be calculated by dividing, by an oscillator index, a value obtained by multiplying an amplitude correction gain, an error value, and a resulting value obtained by applying a phase of an $i^{th}$ oscillator to a sine function. A current amplitude correction value may be calculated by multiplying the amplitude correction quantity by a correction iteration period $T_s$, and adding a previous amplitude correction value to a resulting value of the multiplying. The current amplitude correction value may be restricted not to be less than "0". An error value between the measured joint angle and the overlapping angle may be reduced through Equation 10.

$$\varphi_i(n+1) = \varphi_i(n) + T_g\left(i\omega(n) + k_\varphi \frac{\varepsilon}{\sum \alpha_i(n)} \cos(\varphi_i(n))\right) \quad \text{[Equation 11]}$$

The processor 320 may use Equation 11 to calculate phases of oscillators having an i-fold frequency of a fundamental frequency, among a plurality of oscillators of a PCAO. In Equation 11, $k_\varphi$ denotes a phase correction gain, and ω denotes a fundamental frequency of an AO. The $i^{th}$ oscillator may have the i-fold frequency of the fundamental frequency. A phase increment may vary due to a value obtained by multiplying an error value by a cosine function value. Thus, an error value between an input of an AO and an overlapping angle of the AO may decrease. To correct a phase, a fifth value may be calculated by multiplying an index of an oscillator by a fundamental frequency of the AO.

A sixth value may be calculated by multiplying a phase correction gain, an error, and a resulting value obtained by applying a phase of a corresponding oscillator to a cosine function, and dividing a resulting value of the multiplying by a sum of amplitudes of the plurality of oscillators. A phase correction value of the $i^{th}$ oscillator may be calculated by adding the fifth value and the sixth value. By multiplying the phase correction value by a period of a correction cycle, and adding a previous correction phase to a resulting value of the multiplying, a currently corrected phase of the $i^{th}$ oscillator may be calculated.

$$\omega(n+1) = \omega(n) + \quad \text{[Equation 12]}$$
$$T_g\left(k_\omega \frac{\varepsilon}{\sum \alpha_i} \cos(\varphi_1) + \sum k_e e^{-\frac{(\omega_{ext} - \omega)^2}{2}}(\omega_{ext} - \omega)\right)$$

The processor 320 may use Equation 12 to correct a fundamental frequency of a PCAO. A seventh value may be calculated by multiplying a frequency correction gain, an error value, and a resulting value of applying a phase of a first oscillator to a function with respect to a variation in a reference trajectory. In Equation 12, $k_\omega$ denotes a frequency correction gain, $k_c$ denotes a coupling frequency gain, and $\omega_{ext}$ denotes a frequency of a joint angle trajectory of another leg measured by another PCAO. The seventh value of Equation 12 may be a value to correct the fundamental frequency such that the fundamental frequency of the AO corresponds to a frequency of the trajectory of the measured joint angle. An eighth value may be obtained by adding, with respect to all joints excluding the joint calculated in Equation 12, values of obtained by multiplying a coupling frequency gain, a natural exponential value of a value obtained by multiplying −½ by a square of a difference between a frequency of a joint angle trajectory measured by another PCAO in another aspect and a fundamental frequency of the AO of the present PCAO, and a difference between the frequency of the joint angle trajectory measured in the other aspect and the fundamental frequency. For example, the present PCAO may measure a frequency of an angle trajectory of a hip joint on one side, and the other PCAO may measure a frequency of an angle trajectory of a hip joint on another side.

In general, an estimated frequency of a left joint angle trajectory may coincide with an estimated frequency of a right joint angle trajectory. When the estimated frequencies differs from one another, the eighth value may be a value to correct the fundamental frequency to match the different frequencies. In detail, a natural exponential portion of the eighth value may converge to "0" when the difference between the two frequencies is great. Thus, coupling between the two frequencies may be blocked. The natural exponential portion of the eighth value may induce the two frequencies to be identical to each other when the difference between the two frequencies is modest. A sum of the seventh value and the eighth value may be a correction quantity of the fundamental frequency of the AO. By multiplying the sum of the seventh value and the eighth value by a correction period, and adding a previous correction fundamental frequency to a resulting value of the multiplying, a current correction fundamental frequency may be calculated.

$$\alpha_o(n+1) = \alpha_o(n) + T_s k_o \varepsilon \quad \text{[Equation 13]}$$

The processor 320 may use Equation 13 to correct an offset of an overlapping angle of a PCAO. In Equation 13, $k_o$ denotes an offset correction gain. Using Equation 13, a calculation error resulting from an offset may be reduced by correcting the offset of the overlapping angle of the PCAO to correspond to an offset of a measured joint angle.

$$\varphi_{cc} = \varphi_1 + f(\varphi_1 - \varphi_2) \quad \text{[Equation 14]}$$

The processor 320 may use Equation 14 to calculate a gait phase a current gait cycle based on a first phase and a second phase. By adding, to the first phase, a value obtained by accumulating the phase difference between the first phase and the second phase at each cycle, the gait phase of the gait cycle may be calculated. As the cycle to compensate for the phase difference between the first phase and the second phase is repeated, the phase difference between the first phase and the second phase may converge to a desired value.

Using Equations 8 through 14, the processor 320 acting as the PCAO may obtain the gait phase of the gait cycle corresponding to the reference trajectory and the trajectory of the measured joint angle. The obtained gait phase of the one leg may be, for example, a first gait phase.

In operation 1225, the processor 320 may calculate a gait frequency of another leg using a PSAO of the other leg. Since the descriptions of operation 1220 are also applicable here, repeated descriptions with respect to operation 1225 will be omitted.

In operation 1235, the processor 320 may detect a gait phase of a gait cycle of the other leg based on the gait frequency. Since the descriptions of operation 1230 are also applicable here, repeated descriptions with respect to operation 1235 will be omitted. The detected gait phase of the other leg may be, for example, a second gait phase.

In operation 1240, the processor 320 may compare the first gait phase to the second gait phase. For example, a difference between the first gait phase and the second gait phase may be 50% in a normal gait. In an abnormal gait, the difference between the first gait phase and the second gait phase may not be 50%.

In operation 1245, the processor 320 may set phase offsets for the PSAO of the one leg and the PSAO of the other leg. An angle of 180°, for example, a gait cycle 50% may be set for the normal gait, and a phase offset through which an asymmetric gait cycle is recognizable may be set for the abnormal gait.

Figure 13:
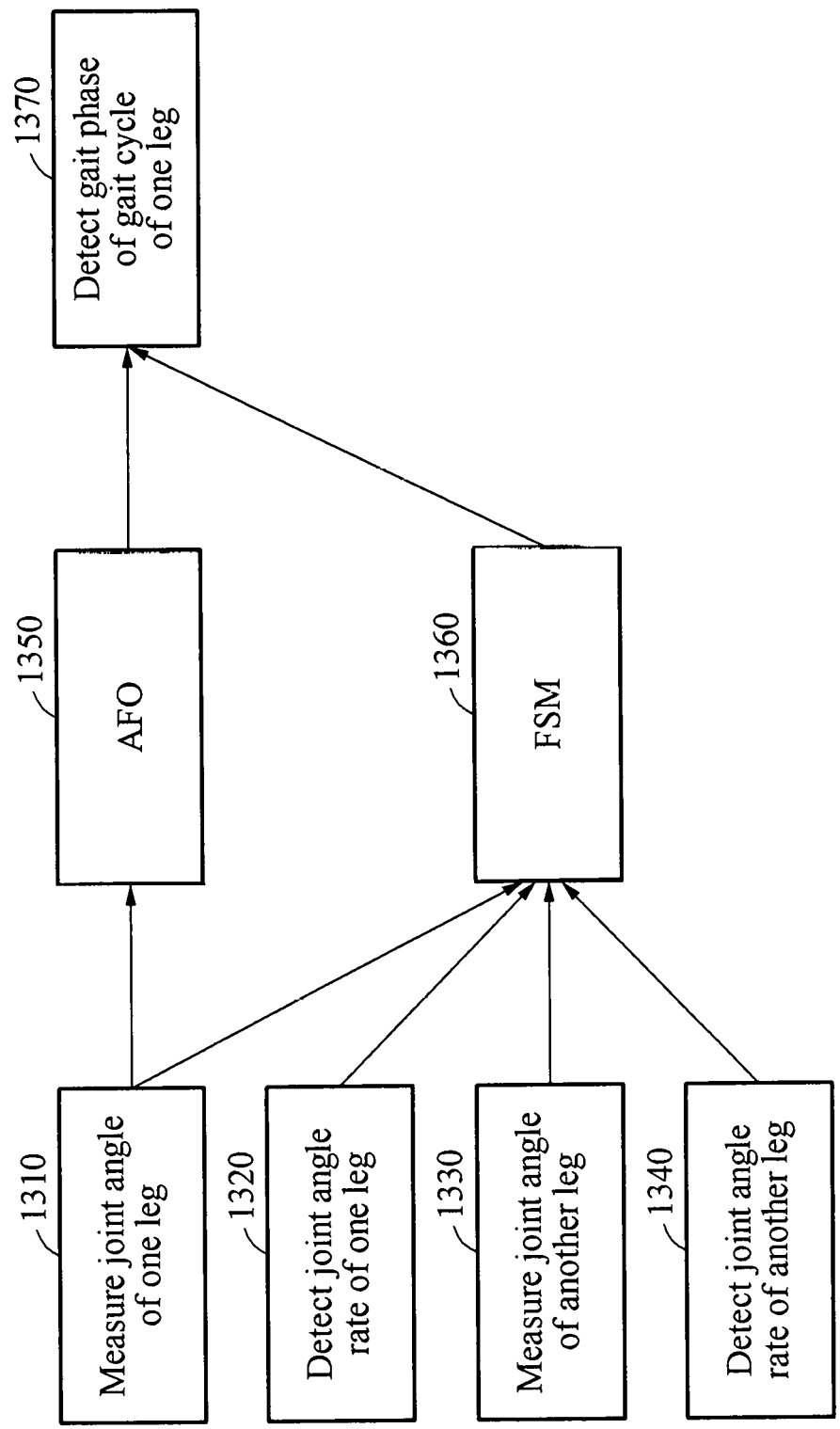
FIG. 13 illustrates an example of a method of detecting a gait phase based on a finite state machine (FSM) and an adaptive frequency oscillator (AFO)

FIG. 13 illustrates an example of a method of detecting a gait phase of a gait cycle based on an FSM and an AFO.

Operation 1110 may include operations 1310 through 1340, and operation 1120 may include operations 1350 through 1370.

In operation 1310, the processor 320 may measure a joint angle of one leg.

In operation 1320, the processor 320 may detect a joint angle rate of the one leg. In operation 1330, the processor 320 may measure a joint angle of another leg. In operation 1340, the processor 320 may detect a joint angle rate of the other leg.

In operation 1350, the processor 320 may calculate a current gait frequency using an AFO. For example, the processor 320 may calculate the current gait frequency based on the joint angle of the one leg.

In operation 1360, the processor 320 may determine a current gait state among preset gait states using an FSM. For example, the processor 320 may determine the current gait state based on the joint angle of the one leg, the joint angle rate of the one leg, the joint angle of the other leg, and the joint angle rate of the other leg. The preset gait states will be described in detail with reference to FIG. 14.

In operation 1370, the processor 320 may detect a gait phase of a gait cycle of the one leg based on at least one of the calculated current gait frequency and the current gait state.

Figure 14:
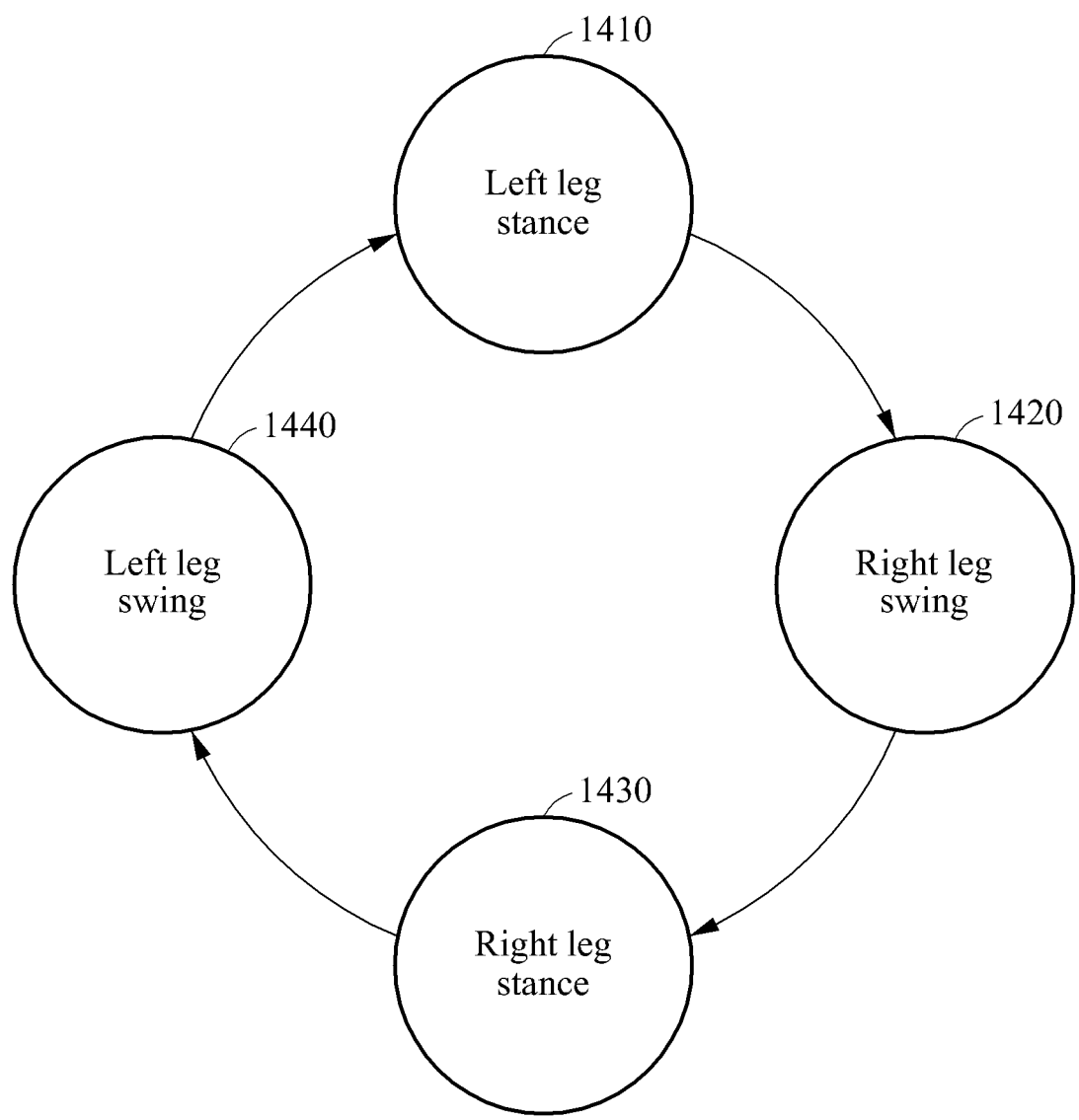
FIG. 14 illustrates an example of transition between gait states.

FIG. 14 illustrates an example of transition between gait states.

In a general gait mechanism, a gait state at a start of a gait may vary. However, a transition among gait states may occur in an order of a left leg stance 1410, a right leg swing 1420, a right leg stance 1430, and a left leg swing 1440. After the left leg swing 1440, the right leg stance 1410 may be performed again.

FIG. 15 illustrates an example of a method of adjusting a timing for outputting a torque to one leg based on a joint angle rate of another leg.

Operation 1510 may be performed in parallel with operations 410 through 430.

In operation 1510, the processor 320 may detect an interval in which a joint angle rate of another leg is maximized. For example, the processor 320 may detect the interval in which the joint angle rate of the other leg is maximized from a trajectory of the joint angle rate measured in a previous gait cycle. The processor 320 may detect a gait phase of the interval in which the joint angle rate of the other leg is maximized.

In operation 440, the processor 320 may adjust a timing for outputting a torque to one leg based on the interval in which the joint angle rate of the other leg is maximized. For example, the processor 320 may adjust a torque output timing of the one leg such that the torque is output at the gait phase of the interval in which the joint angle rate of the other leg is maximized.

Figure 16:
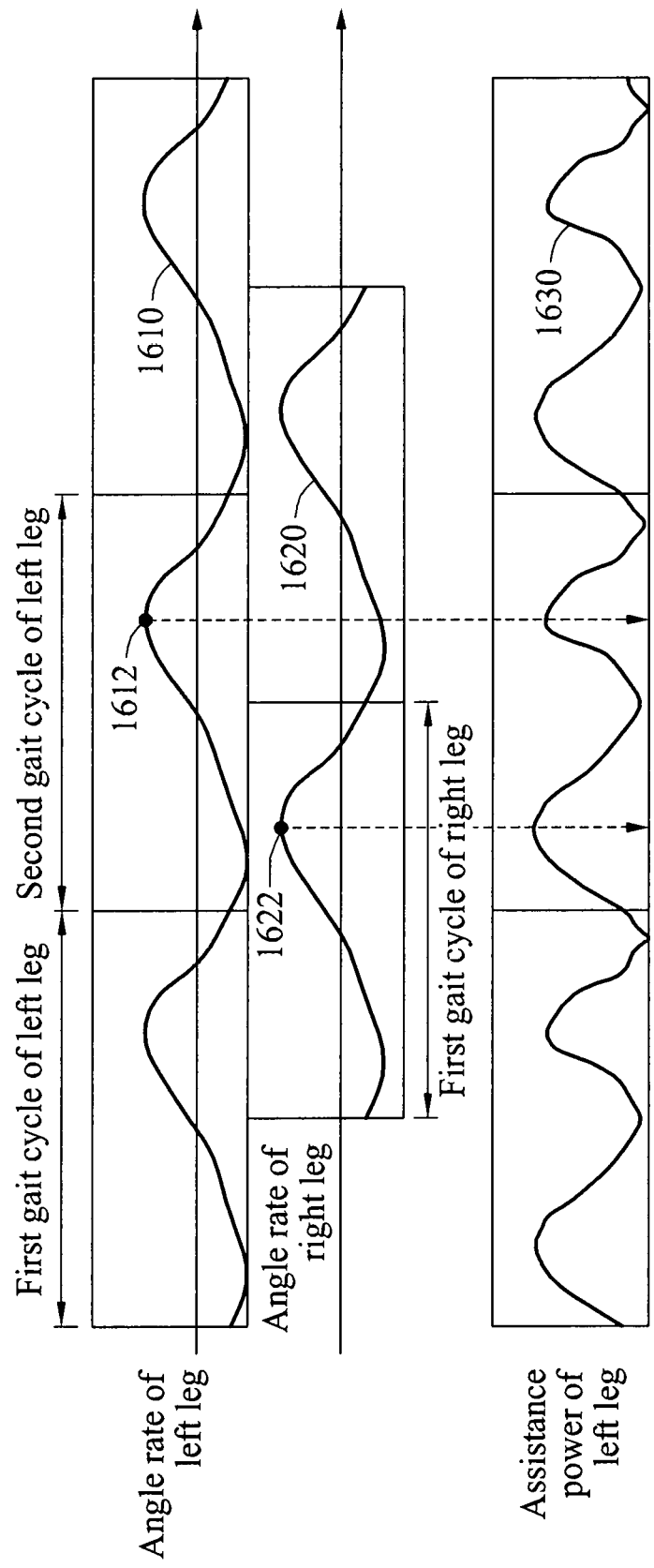
FIG. 16 illustrates an example of an assistance power output to a left leg based on a joint angle rate of the left leg and a joint angle rate of a right leg.

FIG. 16 illustrates an example of an assistance power output to a left leg based on a joint angle rate of the left leg and a joint angle rate of a right leg.

A trajectory 1610 of a joint angle rate of a left leg and a trajectory 1620 of a joint angle of a right leg may be acquired through a plurality of gait cycles. In a normal gait, a difference between the trajectory 1610 and the trajectory 1620 may be an angle of 180°, for example, a gait cycle 50%.

The processor 320 may detect an interval in which a joint angle rate of the left leg is maximized through a first gait cycle of the left leg, and detect a gait phase of the detected interval. The processor 320 may adjust a timing of an output torque output to the left leg such that an assistance power output to the left leg is maximized at a gait phase 1612 of an interval in which the joint angle rate of the left leg is maximized in a second gait cycle.

The processor 320 may detect an interval in which a joint angle rate of the right leg is maximized through a previous gait cycle of the right leg, and detect a gait phase of the detected interval. The processor 320 may adjust the timing of the output torque output to the left leg such that the assistance power output to the left leg is maximized at a gait phase 1622 of an interval in which the joint angle rate of the right leg is maximized in a first gait cycle. For example, the processor 320 may adjust the timing of the output torque output to the left leg such that an assistance power delivered to the left leg is maximized when the right leg is in a swing state and the joint angle rate is maximized in the swing state. By delivering a maximum assistance power to a standing leg when a joint angle rate of a swinging leg is maximized, a gait stability may increase. Concisely, a trajectory 1630 of the assistance power of the left leg may represent a maximum assistance power when the joint angle rate of each of the left leg and the right leg in the swing state is maximized.

Figure 17:
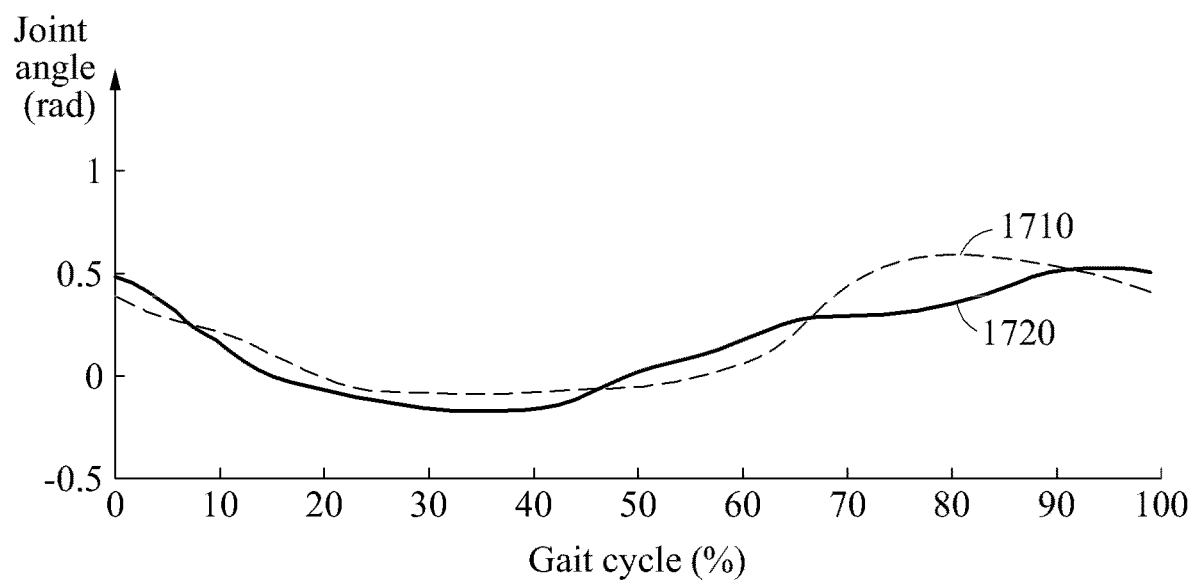
FIG. 17 illustrates an example of a joint angle of an abnormal gait.

FIG. 17 illustrates an example of a joint angle of an abnormal gait.

An abnormal gait may be performed by, for example, a user having a paralyzed leg. A trajectory 1720 of a joint angle of the paralyzed leg may differ from a trajectory 1710 of a joint angle of a leg in a normal state. Hereinafter, the leg in the normal state may also referred to as, for example, a normal leg. A variation in the joint angle of the paralyzed leg may be smaller when compared to the normal leg.

Figure 18:
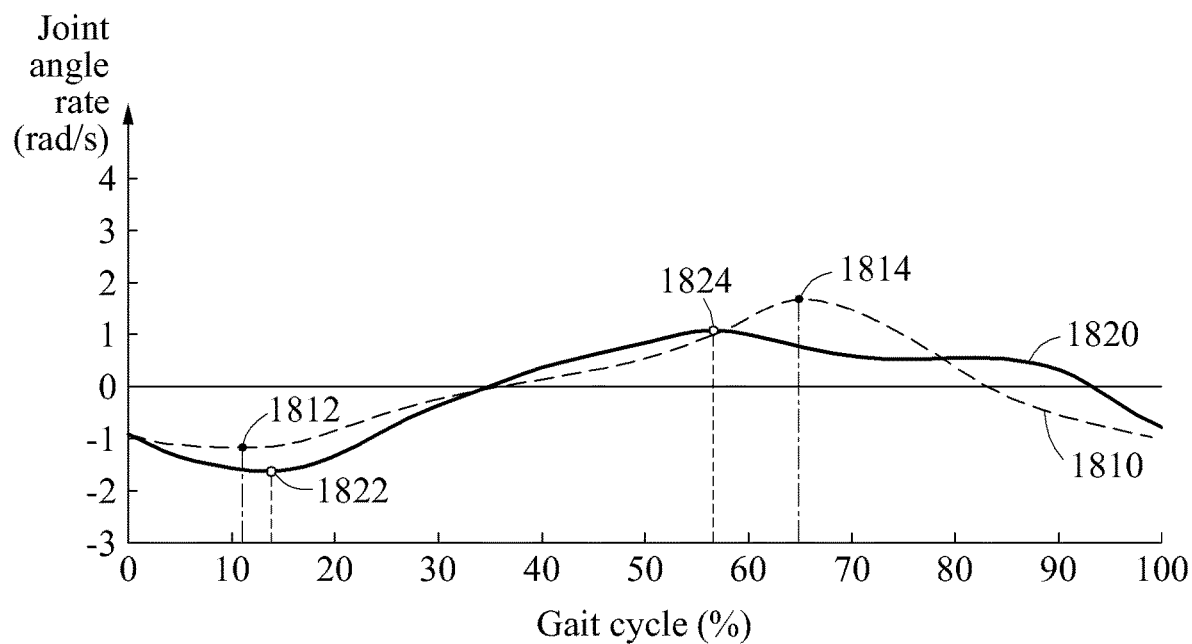
FIG. 18 illustrates an example of a joint angle rate of an abnormal gait.

FIG. 18 illustrates an example of a joint angle rate of an abnormal gait.

A user performing an abnormal gait due to, for example, a paralyzed leg may have a gait pattern in which a swing state of the paralyzed leg is prolonged and a stance of the paralyzed leg is shortened. In response to the prolonged swing state of the paralyzed leg, a stance state of a normal leg may be correspondingly prolonged. Also, in response to the shortened swing state of the paralyzed leg, a swing state of the normal leg may be correspondingly shortened. A difference in phase between intervals 1822 and 1824 in which the joint angle rate of the paralyzed leg is maximized or a difference between gait phases of gait cycles of the intervals 1822 and 1824 may be less than a difference in phase between intervals 1812 and 1814 in which the joint angle rate of the normal leg is maximized or a difference between gait phases of gait cycles of the intervals 1812 and 1814.

In a normal gait, a torque output timing may be adjusted such that a left leg and a right leg have the same gait frequency. However, in the abnormal gait, a phase offset may be set based on an adaptive gait pattern of a user. For example, a phase offset for a leg in an abnormal state may be applied when a gait phase of a gait cycle is detected based on a PSAO of another leg.

Figure 19:
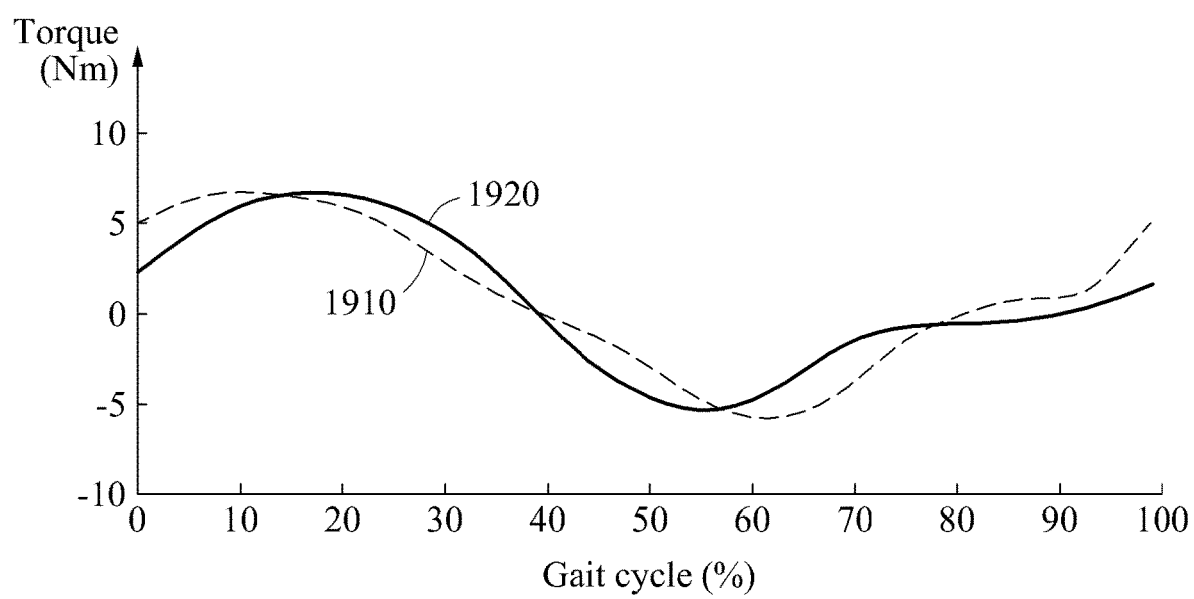
FIG. 19 illustrates an example of an output torque of an abnormal gait.

FIG. 19 illustrates an example of an output torque of an abnormal gait.

FIG. 19 illustrates trajectories 1910 and 1920 of output torques having adjusted timings. A gait phase corresponding to an interval in which a torque output to a leg in an abnormal state is maximized in the trajectory 1920 may outpace a gait phase corresponding to an interval in which a torque output to a leg in a normal state is maximized in the trajectory 1910.

Figure 20:
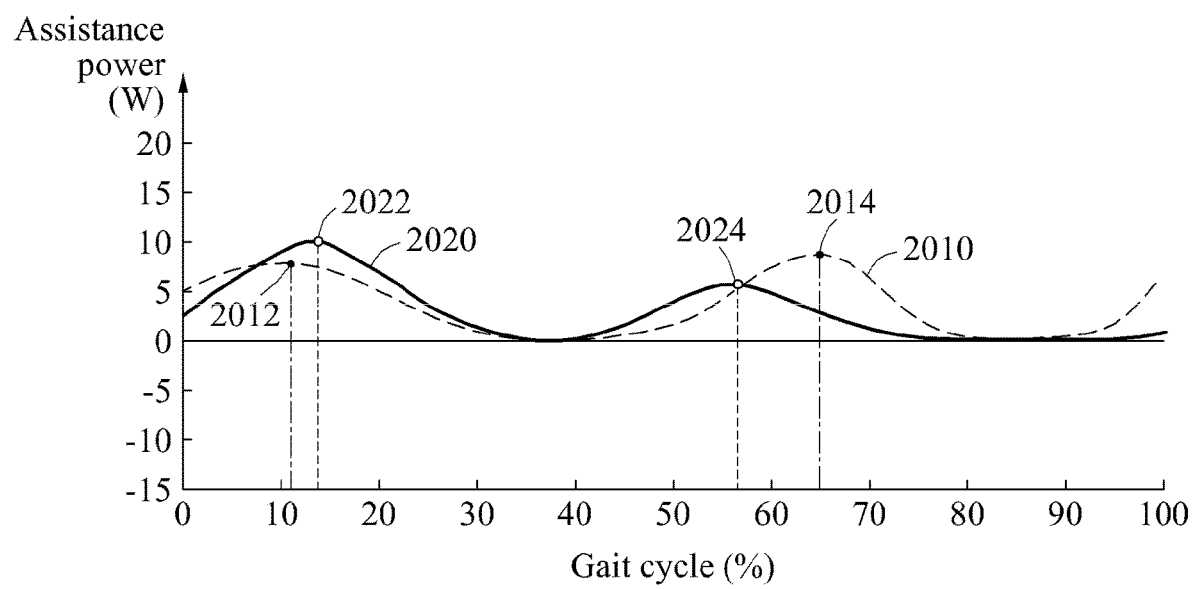
FIG. 20 illustrates an example of an assistance power of an abnormal gait.

FIG. 20 illustrates an example of an assistance power of an abnormal gait.

FIG. 20 illustrates trajectories 2010 and 2020. Each of the trajectories 2010 and 2020 represents an output assistance power calculated based on an output torque having an adjusted timing. A difference in gait phase between intervals 2022 and 2024 in which an output assistance power of a leg in an abnormal state is maximized may be less than a difference in gait phase between intervals 2012 and 2014 in which an output assistance power of a leg in a normal state is maximized.

Gait phases of the intervals 2012 and 2014 in which the output assistance power of the leg in the normal state is maximized may be the same as gait phases of the intervals 1812 and 1814 in which a joint angle rate of the leg in the normal state is maximized. Gait phases of the intervals 2022 and 2024 in which the output assistance power of the leg in the abnormal state is maximized may be the same as gait phases of the intervals 1822 and 1824 in which a joint angle rate of the leg in the abnormal state is maximized.

Figure 21:
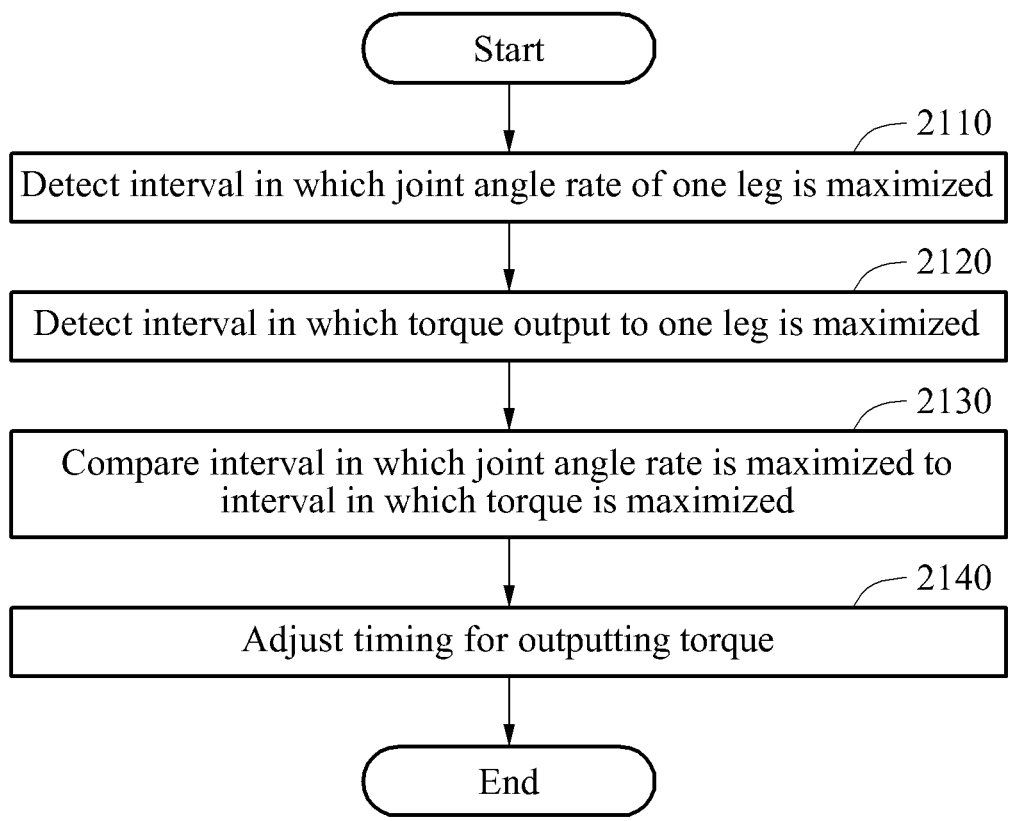
FIG. 21 illustrates another example of a torque output timing adjustment method.

FIG. 21 illustrates another example of a torque output timing adjustment method.

In operation 2110, the processor 320 may detect an interval in which a joint angle rate of one leg is maximized. The descriptions related to operation 410 are also applicable here and thus, repeated descriptions of operation 2110 will be omitted.

In operation 2120, the processor 320 may detect an interval in which a torque output to the one leg is maximized. For example, the processor 320 may acquire a trajectory of an output torque of a previous gait cycle and detect the interval in which the torque output to the one leg is maximized and a gait phase of the interval based on the acquired trajectory.

In operation 2130, the processor 320 may compare the interval in which the joint angle rate is maximized to the interval in which the output torque is maximized. For example, the processor 320 may compare a third gait phase of the interval in which the joint angle rate is maximized to a fourth gait phase of the interval in which the output torque is maximized. The processor 320 may compare the third gait phase to the fourth gait phase and also calculate a difference between the third gait phase and the fourth gait phase.

In operation 2140, the processor 320 may adjust a timing for outputting the torque to the one leg based on a comparison result. As an example, the processor 320 may adjust a torque output timing such that the third gait phase matches the fourth gait phase. As another example, the processor 320 may adjust the torque output timing such that a difference between the third gait phase and the fourth gait phase corresponds to a preset difference.

The units and/or modules described herein may be implemented using hardware components and software components. For example, the hardware components may include microphones, amplifiers, band-pass filters, audio to digital convertors, and processing devices. A processing device may be implemented using one or more hardware device configured to carry out and/or execute program code by performing arithmetical, logical, and input/output operations. The processing device(s) may include a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciate that a processing device may include multiple processing elements and multiple types of processing elements. For example, a processing device may include multiple processors or a processor and a controller. In addition, different processing configurations are possible, such a parallel processors.

The software may include a computer program, a piece of code, an instruction, or some combination thereof, to independently or collectively instruct and/or configure the processing device to operate as desired, thereby transforming the processing device into a special purpose processor. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A method of adjusting a torque output timing of a torque output by a walking assistance apparatus to a leg of a user, the method comprising:
   detecting a joint angle rate interval in which a joint angle rate of the leg of the user is maximized in a gait cycle of the leg;
   detecting an assistance power interval in which an assistance power applied from the walking assistance apparatus to the leg is maximized in the gait cycle; and
   adjusting a timing for outputting a torque to the leg based on the joint angle rate interval and the assistance power interval such that a difference between the joint angle rate interval and the assistance power interval is equal to a predefined offset.

2. The method of claim 1, further comprising:
   measuring a joint angle of the leg;
   detecting a gait phase of the leg based on the joint angle; and
   calculating the torque based on the gait phase.

3. The method of claim 2, wherein the detecting of the gait phase comprises:
   detecting the gait phase based on the joint angle and a particularly shaped adaptive oscillator (PSAO) model of the leg.

4. The method of claim 3, wherein the leg of the user is a first leg of the user, and the detecting of the gait phase comprises:
   detecting the gait phase based on a joint angle of a second leg and a PSAO model of the second leg of the user.

5. The method of claim 2, wherein the detecting the gait phase comprises:
   detecting the gait phase based on the joint angle and a finite state machine (FSM) model of the leg.

6. The method of claim 2, wherein the detecting the gait phase comprises:
   detecting the gait phase based on the joint angle, a finite state machine (FSM) model of the leg, and an adaptive frequency oscillator (AFO) model of the leg.

7. The method of claim 1, wherein the detecting the assistance power interval comprises:
   detecting the torque output to the leg;
   detecting the joint angle rate associated with the leg;
   calculating the assistance power based on the torque and the joint angle rate; and
   detecting the assistance power interval as an interval in which the assistance power is maximized in the gait cycle.

8. The method of claim 7, wherein the detecting the joint angle rate comprises:
   detecting the joint angle rate using an angle rate sensor.

9. The method of claim 7, wherein the detecting the joint angle rate comprises:
   detecting the joint angle rate based on a joint angle measured using an angle sensor.

10. The method of claim 7, wherein the detecting the torque comprises:
    detecting the torque using a torque sensor.

11. The method of claim 7, wherein the detecting the torque comprises:
    measuring, via a current sensor, a current flowing in a motor of the walking assistance apparatus;
    calculating an initial torque output by the motor based on the current; and
    calculating the torque based on the initial torque and a dynamic model of the walking assistance apparatus.

12. The method of claim 1, wherein the detecting the joint angle rate interval comprises:
    detecting an interval in which the joint angle rate is maximized when the leg is in a stance state; and
    detecting an interval in which the joint angle rate is maximized when the leg is in a swing state.

13. The method of claim 1, wherein the adjusting further comprises:
    adjusting the timing such that the joint angle rate interval matches the assistance power interval, if the joint angle rate interval differs from the assistance power interval.

14. The method of claim 1, the leg of the user is a first leg of the user, and the method further comprises:
    detecting a joint angle rate interval in which a joint angle rate of a second leg of the user wearing the walking assistance apparatus is maximized in a gait cycle of the second leg,
    wherein
    the adjusting adjusts the timing based on the joint angle rate interval of the first leg, the assistance power interval, and the joint angle rate interval of the second leg.

15. A torque output timing adjustment apparatus comprising:
    a sensor configured to measure a joint angle rate of a leg of a user wearing a walking assistance apparatus; and
    a processor configured to,
    detect a joint angle rate interval in which the joint angle rate of the leg is maximized in a gait cycle of the leg,
    detect an assistance power interval in which an assistance power applied from the walking assistance apparatus to the leg is maximized in the gait cycle, and
    adjust a timing for outputting a torque to the leg such that a difference between the joint angle rate interval and the assistance power interval is equal to a predefined offset.

16. The torque output timing adjustment apparatus of claim 15, wherein
    the sensor is configured to measure a joint angle of the leg, and
    the processor is configured to,
    detect a gait phase of the leg based on the joint angle, and
    calculate the torque based on the gait phase.

17. The torque output timing adjustment apparatus of claim 15, wherein the processor is configured to,
    detect the torque output to the leg,
    detect the joint angle rate of the leg,
    calculate the assistance power based on the torque and the joint angle rate, and
    detect the assistance power interval as an interval in which the assistance power is maximized in the gait cycle.

18. A method of adjusting a torque output timing of a torque output by a walking assistance apparatus to a leg of a user, the method comprising:
    detecting a joint angle rate interval in which a joint angle rate of the leg of the user is maximized in a gait cycle of the leg;
    detecting a torque interval in which a torque applied from the walking assistance apparatus to the leg is maximized in the gait cycle; and
    adjusting a timing for outputting the torque to the leg based on the joint angle rate interval and the torque interval such that a difference between the joint angle rate interval and the torque interval is equal to a predefined offset.

\* \* \* \* \*